US011246664B2

(12) United States Patent
Andrews et al.

(10) Patent No.: US 11,246,664 B2
(45) Date of Patent: Feb. 15, 2022

(54) ASTIGMATISM CORRECTION

(71) Applicants: Carl Zeiss Meditec AG, Jena (DE); Carl Zeiss Meditec Inc., Dublin, CA (US)

(72) Inventors: Delbert Peter Andrews, Oberkochen (DE); Kyle Hunter Smith, Temple, TX (US); Jeremiah Robert Elliott, Temple, TX (US)

(73) Assignee: CARL ZEISS MEDITEC AG, Jena (DE)

( * ) Notice: Subject to any disclaimer, the term of this patent is extended or adjusted under 35 U.S.C. 154(b) by 237 days.

(21) Appl. No.: 16/419,064

(22) Filed: May 22, 2019

(65) Prior Publication Data
US 2019/0357980 A1    Nov. 28, 2019

Related U.S. Application Data

(60) Provisional application No. 62/750,270, filed on Oct. 25, 2018.

(30) Foreign Application Priority Data

May 22, 2018 (DE) .......................... 102018208014.3

(51) Int. Cl.
A61B 34/10    (2016.01)
A61F 2/16    (2006.01)
(Continued)

(52) U.S. Cl.
CPC .............. A61B 34/10 (2016.02); A61B 3/102 (2013.01); A61B 3/1005 (2013.01);
(Continued)

(58) Field of Classification Search
CPC ....... A61B 34/10; A61B 90/20; A61B 3/1015; A61B 3/102; A61B 3/145; A61B 3/1005;
(Continued)

(56) References Cited

U.S. PATENT DOCUMENTS

2012/0296321 A1*  11/2012  Frey .................... A61F 9/00827
                                                          606/5
2014/0066835 A1*   3/2014  Muller .................. A61F 9/013
                                                          604/20

(Continued)

FOREIGN PATENT DOCUMENTS

WO    WO 2018052455 A1    3/2018

OTHER PUBLICATIONS

Wikipedia, "Mathematical Optimization", Feb. 10, 2018, pp. 1-12.

Primary Examiner — Mohammed A Hasan
(74) Attorney, Agent, or Firm — Leydig, Voit & Mayer, Ltd.

(57) ABSTRACT

A therapeutic method can include receiving an initial astigmatism condition of an eye; receiving a target final astigmatism condition of the eye; generating, based on the initial and target final astigmatism conditions, an eye incision pattern by iterating through a plurality of potential corrective combinations; and cutting the eye based on the eye incision pattern. Each of the potential corrective combinations can be defined by one or more of: an intraocular lens selected from a plurality of intraocular lens options, an access incision selected from a plurality of access incision options, and an arcuate incision selected from a plurality of arcuate incision options.

20 Claims, 7 Drawing Sheets

(51) Int. Cl.
*A61F 9/008* (2006.01)
*A61B 90/20* (2016.01)
*A61B 3/10* (2006.01)
*A61B 3/14* (2006.01)
*A61B 8/10* (2006.01)
*A61B 3/117* (2006.01)
*A61B 3/103* (2006.01)
*A61B 90/00* (2016.01)

(52) U.S. Cl.
CPC .......... *A61B 3/1015* (2013.01); *A61B 3/1035* (2013.01); *A61B 3/117* (2013.01); *A61B 3/145* (2013.01); *A61B 8/10* (2013.01); *A61B 90/20* (2016.02); *A61F 2/1662* (2013.01); *A61F 9/008* (2013.01); *A61B 2034/104* (2016.02); *A61B 2090/373* (2016.02); *A61B 2505/05* (2013.01); *A61F 2009/0088* (2013.01)

(58) Field of Classification Search
CPC ......... A61B 8/10; A61B 3/117; A61B 3/1035; A61B 2505/05; A61B 2034/104; A61B 2090/373; A61F 2/1662; A61F 9/008; A61F 2009/0088; A61F 2009/00878
USPC ........................................................ 351/246
See application file for complete search history.

(56) References Cited

U.S. PATENT DOCUMENTS

2015/0046094 A1   2/2015  Chaudhary et al.
2016/0089271 A1*  3/2016  Zacharias ........... A61F 9/00825
                                                    606/5

\* cited by examiner

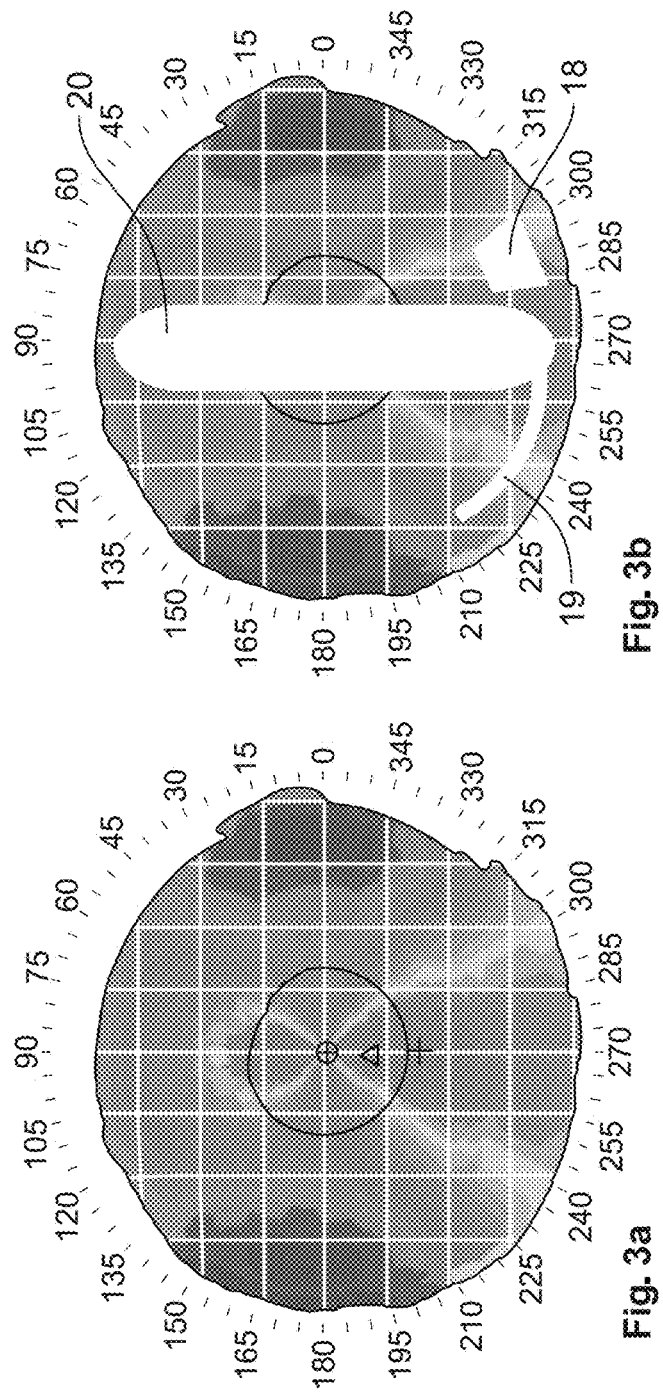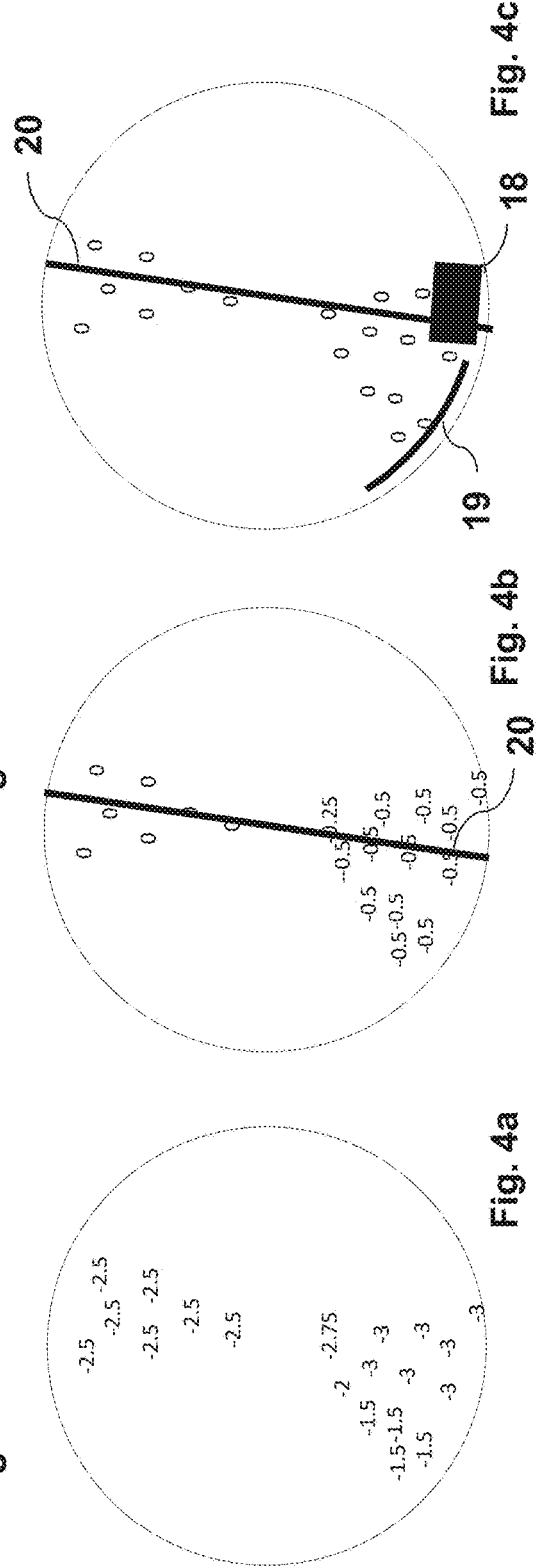

Fig. 7

ASTIGMATISM CORRECTION

CROSS-REFERENCE TO PRIOR APPLICATIONS

Priority is claimed to German Patent Application No. 10 2018 208 014.3 (filed on May 22, 2018) and U.S. Provisional Patent Application No. 62/750,270 (filed on Oct. 25, 2018), which are each hereby incorporated by reference in their entirety.

TECHNICAL FIELD

Embodiments of the present disclosure relate, among other things, to astigmatism correction. The correction can occur during cataract surgery.

BACKGROUND

The eyes of many humans have an astigmatism that is pronounced to a greater or lesser extent. As a result of corneal distortions that allow a plane of incidence with maximum curvature of the corneal surface and hence maximum refractive power and a plane of incidence with minimum curvature and hence minimum refractive power to be established for the corresponding eye, the light rays emanating from an observed object are not focused at a point on the retinal plane but, instead, are imaged along a focal line. A light ray that is incident in the eyeball of the eye in a manner parallel to the optical axis is refracted to a different extent depending on its plane of incidence formed with the optical axis. The difference between these two so-called principal meridians, i.e., the plane with maximum curvature and the plane with minimum curvature, is referred to as the strength of the astigmatism. If the cornea of the eye has irregular curvature, these two planes do not lie perpendicular to one another; this being referred to as an irregular astigmatism. By contrast, the planes of maximum corneal curvature and of minimal corneal curvature are perpendicular to one another in the case of a regular astigmatism.

The astigmatism of a patient's eye can be reduced by targeted correction incisions in the cornea of the eye, as described in US 2008/0275433 A1. Such astigmatism correction incisions in the cornea are usually implemented in conjunction with other refractive error correction incisions in the cornea of the patient's eye. Refractive error corrections are only correction incisions in the cornea which do not cut through the entire cornea.

Cataract-surgical measures are the surgical measures in ophthalmology that are carried out most worldwide. Here, a natural lens of a patient's eye, which has become opaque over the years, is emulsified by means of ultrasound and/or fragmented by means of a focused laser beam, aspirated via an access incision (also called "phacoemulsification incision" or "phaco incision", PI) in the cornea and replaced by an intraocular lens. The incisions in the cornea for producing an access (and also capsulotomy or capsulorhexis for opening the capsular bag) can be produced manually or else by means of a laser therapy apparatus, which comprises a pulsed laser, in particular a femtosecond or picosecond laser, for "cutting" the tissue of the patient's eye by means of photodisruption, or else manually by way of a corresponding surgical knife. Thus, in principle, the most important "optically effective" elements of the eye, i.e., the cornea and the lens, are "processed" within the scope of a cataract operation, which is why this lends itself also to at least partly correcting refractive errors. In particular, correcting the astigmatism plays an important role—both the natural astigmatism and the additional surgically induced astigmatism together.

Initially, the opaque natural lens of the patient's eye can be replaced within the scope of a cataract operation by such an intraocular lens that counteracts the specific astigmatism of said patient's eye, i.e., the specific, non-rotationally symmetric corneal curvature thereof. The regular component of the astigmatism can thus be initially corrected by means of toric intraocular lenses, which have a plane of maximum curvature and, perpendicular thereto, a plane of minimum curvature.

However, incisions implemented in the cornea lead to asymmetry—provided they are not implemented in symmetric fashion—and hence lead to a surgically induced astigmatism. It is known that such incisions, as have to be made within the scope of cataract surgery for the purposes of establishing an access, influence the astigmatism and, in particular, the irregular astigmatism of a patient's eye. In the positive case, where an access incision is placed correctly, the irregular astigmatism can be significantly reduced by the access incision on its own. By contrast, the irregular astigmatism of the patient's eye is increased in the case of a disadvantageous placement of the access incision.

Modern cataract surgeons strive to minimize postoperative astigmatism as a means of improving their patient's postoperative uncorrected visual acuity. More than 70% of all eyes that have cataract surgery have significant astigmatism that could decrease postoperative uncorrected visual acuity if not managed appropriately.

Further, arcuate incisions at different positions of the patient's eye allow a pre-existing and/or surgically induced astigmatism to be at least partly compensated again or allow a residual astigmatism that exists after the access incision to be reduced further.

Arcuate incisions in the cornea made in conjunction with the cataract surgery are a widely accepted method of correcting or reducing postoperative corneal astigmatism. These can be performed manually with a knife blade, or with a femtosecond laser. Various factors are believed to be associated with the effectiveness of arcuate incisions including the number of arcs, arc length, incision depth, and optical zone (diameter) of the arcuate incisions. Surgeons must plan these incisions preoperatively, but cannot be certain of the results until several weeks after the surgery is completed. Although arcuate incisions are effective, the results have been much less predictable than toric intraocular lenses.

Experienced eye surgeons know approximately where the appropriate incisions have to be placed when they see the astigmatism data of the specific patient eye. According to the prior art, work is then carried out in such a way that the corneal astigmatism of the patient's eye is determined by characterization of the anterior corneal surface (e.g. through keratometry or corneal topography) and often the posterior corneal surface (through OCT or Scheimpflug analysis) an intraocular lens then is initially selected by the surgeon, the access incision is placed at the most probable position and with most probable geometry according to the experience of the surgeon, the natural lens of the patient's eye is removed and the intraocular lens is inserted, arcuate incisions are placed at the most probable position and with the most probable geometry according to the experience of the surgeon. After implantation of the IOL, the surgeon may check the resulting astigmatism using intraoperative keratometry or interoperative aberrometry and correct it where necessary. The surgeon can be assisted by calculation tools, which calculate a residual astigmatism to be expected for the specific parameters of an intraocular lens, of an access incision and of arcuate incisions, as selected by the surgeon.

Cataract surgeons have historically relied on published nomograms that help them plan arcuate incisions. The most popular, and oldest, of these nomograms were created for manual arcuate incisions made near the limbus of the eye, often called limbal relaxing incisions (LRI). These manual nomograms were designed to be simple to remember and did not require digital technology for computation. Other nomograms have been published for use with femtosecond lasers. These include parameters for depth as a percentage of corneal thickness and optical zone as a diameter—irrespective of the diameter of the cornea. Some of these nomograms have been coded into digital systems that can be accessed online, or as a feature of a femtosecond laser system. The more sophisticated digital systems allow surgeons to enter access incision size and location as data elements. The algorithm will adjust the arcuate incision plan by converting it to a single incision rather than a paired incision if the access incision and the originally planned arcuate incision overlap. Overlapping incisions can cause wound leaks and should be avoided. Unfortunately, single incisions may not be able to fully correct the eye's astigmatic error, and may not be the best means of eliminating the overlap. Most relevant nomograms to be used for astigmatism correction are: the Donnenfeld nomogram, the Nichamin nomogram, the Oshika nomogram, the Lindstrom nomogram, and nomograms behind the calculation tool at "Laserarcs.com" and "LRIcalculator.com".

US 2014/0125949 A1 describes a corresponding procedure, in which the development of the astigmatism of the patient's eye is tracked and corrected within the course of the cataract surgery, with an astigmatism axis and its changes during the course of the surgical method being determined to this end.

Here, maintaining control of the development of the astigmatism is substantially more difficult in cataract surgery than within the scope of pure corrections of the cornea, as the influencing quantities are more varied. Also, the possibilities and restrictions of the astigmatism correction differ depending on the variant of the cataract operation—manually or by means of a laser therapy apparatus.

SUMMARY

According to a disclosed embodiment, a therapeutic method can include receiving an initial astigmatism condition of an eye; receiving a target final astigmatism condition of the eye; generating, based on the initial and target final astigmatism conditions, an eye incision pattern by iterating through a plurality of potential corrective combinations; and cutting the eye based on the eye incision pattern. Each of the potential corrective combinations can be defined by one or more of: an intraocular lens selected from a plurality of intraocular lens options, an access incision selected from a plurality of access incision options, and an arcuate incision selected from a plurality of arcuate incision options.

BRIEF DESCRIPTION OF DRAWINGS

Embodiments of the present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following:

FIGS. 3a and 3b show an illustration of the astigmatism measurement, the position of the intraocular lens and possible incisions in a patient's eye FIGS. 4a, 4b and 4c show a further illustration of the astigmatism measurement of a patient's eye, and the effect of correction measures

FIG. 7 shows the principle of conflict avoidance.

DETAILED DESCRIPTION

Figure 1A:
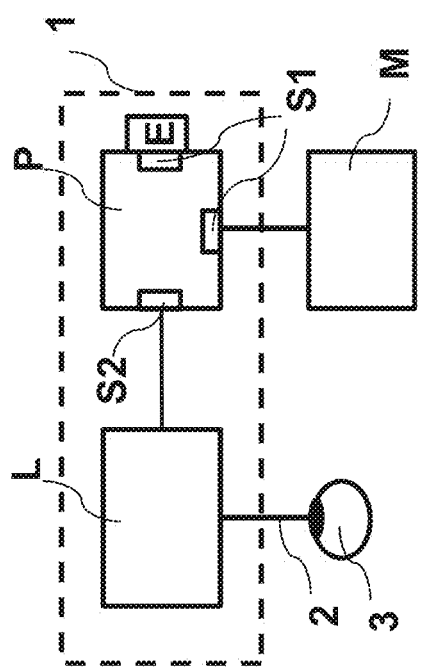
FIG. 1a shows a diagram of a first ophthalmic laser therapy apparatus comprising a first planning device.

Disclosed, among other things, are a planning device (i.e., a system) and a planning method for establishing an astigmatism correction in cataract surgery, in which characterization data of the patient's eye and target data relating to the residual astigmatism, to the variant of the intervention and/or to the precision of the intervention can be supplied and which is configured to produce a pattern of an overall incision geometry at least of access incision and arcuate incisions in the cornea of the patient's eye therefrom. It moreover relates to an ophthalmic laser therapy apparatus comprising such a planning device, and a computer program product.

Therefore, the present application describes a planning device for establishing an astigmatism correction and a corresponding method, by means of which an ideal correction (in general a reduction as far as possible) of the astigmatism of a patient's eye during a cataract operation is facilitated and incisions that inadvertently make the astigmatism worse are avoided.

A planning device for establishing an astigmatism correction in cataract surgery can contain an interface for supplying characterization data of a patient's eye, comprising data about an astigmatism of the patient's eye, and an interface for supplying target data, comprising a maximum (target) residual astigmatism and a variant of cataract-surgical intervention and/or data relating to the precision of this cataract-surgical intervention.

The path of the characterization data and the target data to the interface can be varied: By way of example, the characterization data can be obtained by one or more measuring apparatuses for characterizing the patient's eye and can initially be subject to intermediate processing or else be supplied directly into the planning device from the measuring apparatus. By way of example, the target data can be supplied manually by an input unit of the interface of the planning apparatus, or else can be gathered from feedback from coupling the planning apparatus to a laser therapy apparatus or a surgical microscope. The interface for supplying the characterization data and the interface for supplying the target data need not necessarily differ from one another in this case: optionally, the data can be supplied in succession by the same interface.

The planning device is designed to assist cataract surgeons with arcuate incision planning. It can be adapted for use as a stand-alone device and application, so that it receives measurement data and other target data from "outside" and "exports" the resulting pattern. In this case it can be designed to run in an internet browser environment or in a traditional server-based installation. But preferably it is incorporated into the a general planning device, that might also be part of a controller, for e.g. a therapy system and/or surgical microscope, so that the relevant data points (anterior and posterior keratometry, surgically induced astigmatism, corneal pachymetry, white-to-white measurements, and patient age) are automatically incorporated into the application by internal means like an electronic medical record (EMR) interface and digital equipment interfaces) so that no additional external data entry is required to plan arcuate incisions.

To categorize, the data input can be carried out by: (i) An electronic medical record (EMR) interface: The planning device imports specific data elements through a digital interface with the user's EMR system. (ii) Diagnostic device interfaces: The planning device interfaces with multiple measuring devices (diagnostic devices) and imports specific discrete data characterization directly from those devices. (iii) Manual data entry by the user, e.g. the surgeon.

A residual astigmatism after establishing an astigmatism correction with the planning device must be smaller than a maximum target residual astigmatism value, provided a specific value is entered here. As an alternative to a specific value, entering a general instruction in relation to the residual astigmatism is also possible, such as instructions for "searching the smallest possible residual astigmatism", for example.

The further supplied target data relating to the variant of a cataract-surgical intervention and/or relating to the precision of this cataract-surgical intervention determine the variation possibilities for the embodiment of incisions to be established.

From the supplied data, i.e., the characterization data and the target data, the planning device is embodied to produce a pattern of an overall incision geometry of all incisions which are required in the cornea of the patient's eye for solving the specific problem of the patient's eye, i.e., at least the cataract problem, implementing an astigmatism correction in the process. The pattern should subsequently be carried out. Within the scope of this description, the cornea also contains the limbus as transition region between cornea and sclera: thus, the pattern can be produced in the interior of the cornea and/or in the limbal region. Incisions of the type required here are preferably arranged in the outer region of the cornea or directly in the limbus, i.e., the transition region between cornea and sclera, because they can develop a desired effect here, without at the same time interfering with the vision of the patient.

This pattern of the overall incision geometry therefore comprises at least the position (relative to the structures of the patient's eye) and the geometric data (i.e., the form, an incision width and an incision length, for example) of an access incision and an arcuate incision or a plurality of arcuate incisions. An access incision usually serves to remove the emulsified natural lens of the patient's eye and to introduce a folded intraocular lens (IOL). An arcuate incision (also referred to as "limbal relaxing incision" when done in the limbal region) serves to correct the net astigmatism that is composed of the natural astigmatism (anterior and posterior surfaces) and the surgically induced astigmatism: There is a change in the corneal curvature by placing such arcuate incisions (as is generally the case when placing incisions in the cornea of the patient's eye). Moreover, the pattern of the overall incision geometry may also comprise further data for incisions or modifications (local modifications in the refractive index and/or the elasticity) of the cornea that are required for correcting the patient's eye and that optionally influence the astigmatism of the patient's eye.

The astigmatism modified by the access incision would already count as a surgically induced astigmatism when considering the steps in succession, as has been conventional until now. An arcuate incision or else a plurality of arcuate incisions can be used to correct this as well as the cornea's natural, pre-existing, astigmatism.

Consequently, the overall incision geometry describes the sizes and the shapes of the incisions in relation to one another and in relation to the patient's eye in the totality thereof, said incisions comprising at least one access incision and one or more arcuate incisions.

Furthermore, the planning device can be embodied to produce instructions for the use of a specific intraocular lens, which comprise a type of intraocular lens and an orientation of said intraocular lens in the patient's eye. The type of intraocular lens includes its power and information relating to the correction of a regular component of the astigmatism of the patient's eye, i.e., the toric properties of the lens, and, in particular, when instructed to use a tonic intraocular lens, the orientation thereof in the patient's eye. Optionally, it is possible to resort to a set of intraocular lenses produced as a standard (made available from a database) or else such a lens can be custom produced for the patient from the information relating to the power and the toric properties of the required intraocular lens.

The planning device can be configured or encoded to establish, by way of an iterative method and in each step a corrective effect of a combination of: (i) an intraocular lens and its orientation from a multiplicity of available intraocular lenses, (ii) an access incision and its position (in the cornea including the limbus) from a multiplicity of available variants of an access incision, and (iii) one or more arcuate incisions and their position from a multiplicity of available variants of one or more arcuate incisions. The method can be performed on the astigmatism present in the patient's eye (and take account of an additional surgically induced astigmatism of the patient's eye, i.e., the interaction of the incisions) to determine the residual astigmatism therefrom.

The available variants of the access incision and of the one or more arcuate incisions available to this end are assigned here to the variant of the cataract-surgical intervention and/or the data relating to the precision of the cataract-surgical intervention as well as to the characteristics of the patient's corneal astigmatism: By way of example, if the access incision and the arcuate incisions are implemented manually, the maximum number of possible variations of parameters for relaxation incisions is lower than for incisions carried out by an ophthalmic laser therapy apparatus. The incision width thereof cannot be implemented in variable fashion by hand, and no inclination, or at best a very approximate inclination, is able to be set in relation to the corneal surface, an incision depth is not able to be set accurately, and a minimum incision length will be greater than in the case of incisions implemented by means of an ophthalmic laser therapy apparatus. The number of steps to be tested between various incision lengths and their position in relation to one another and in relation to structures of the eye is significantly greater when the incisions are implemented manually than when the incisions are implemented by means of the ophthalmic laser therapy apparatus. Special incision forms, such as intrastromal incisions, for example, can only be taken into account in the case of an implementation by means of an ophthalmic laser therapy apparatus. Therefore, the number of variable parameters and their gradations will be significantly larger in the case of an implementation by means of an ophthalmic laser therapy apparatus than in the case of a manual implementation of these incisions.

In addition to the characterization of the anterior and posterior corneal surfaces, further concrete data elements influencing an astigmatism correction include one or more of: —Patient age (years)—Patient sex—Patient ethnicity—Peripheral corneal thickness, typically derived from pachymetry—White-to-white (WTW) distance, which is a measurement of the corneal horizontal diameter, typically derived from optical biometry measurements. —Axial Length (AL), which determines the "length" of the patient's eye—Anterior chamber depth (ACD)—Measured anterior corneal curvature—Measured or theoretical posterior corneal curvature—Residual astigmatism after planned cataract surgery with or without a toric IOL –Laterality of proposed surgery (right or left eye)—Access Incision (Phaco incision) length (mm)—Default access incision meridian (degrees), and—Surgeon-individual correction factors.

By systematically trying out all combinations and thereby using the computing speed of modern computer systems possible today to accelerate the finding of results, preferably for a certain selection of a variation parameters in the direction in which the residual astigmatism becomes smaller, a combination is finally found for which the residual astigmatism is smaller than or equal to the maximum residual astigmatism given above. Such a combination is a correction combination. Once such a correction combination has been found, the iterative method can be terminated. This correction combination is then saved as the pattern of the overall incision geometry and the instructions for the use of the specific intraocular lens.

Should the astigmatism correction be established for manual creation of the access incision and the arcuate incisions, the number and the geometrically possible variants of arcuate incisions and the geometry of the access incision are limited, possibly facilitating a faster calculation through the entire trial option space of intraocular lenses, access incision and arcuate incisions. However, a maximum residual astigmatism for a manual incision may possibly need to be set higher than in the case of incisions by means of an ophthalmic laser therapy apparatus. If the maximum residual astigmatism is selected to be too low and, in the process, the possible selection of the parameters of intraocular lens, access incision and arcuate incisions is too restricted on account of limited embodiment options, it will not be possible to specify a correction combination. If such a situation arises (e.g., in the case of very complicated astigmatism configurations), a change of the surgical method from a manual to automated method with the aid of an ophthalmic laser therapy apparatus should be considered.

Preferably, the planning device moreover may contain an interface for outputting control data to a control unit of an ophthalmic laser therapy apparatus in order to control the latter and/or for outputting control data to a control unit of an indication apparatus for the purposes of establishing control data for an astigmatism correction. Such an indication apparatus can be a visual indication apparatus, such as a screen of a surgical microscope or of a video microscope for observing the patient's eye or an external screen, during the cataract-surgical intervention, by means of which the patient's eye, too, can be displayed, preferably in real time. However, this may also be an indication apparatus for text indication or an indication apparatus for acoustic indications.

Moreover, the planning device then can be configured to establish from the pattern of the overall incision geometry control data for an ophthalmic laser therapy apparatus for producing this overall incision geometry and/or control data for creating a pictorial indication of the overall incision geometry on an indication apparatus, in particular on an indication apparatus of a surgical microscope or a video microscope, for overlay purposes on an image of the patient's eye, the ophthalmic laser therapy apparatus being controllable in such a way and/or the pictorial indication of the overall incision geometry on the indication apparatus being overlaid on a real established image of the patient's eye by means of said control data in such a way that the overall incision geometry is producible by cutting along the pattern.

The latter means that the production can be implemented either in automated fashion with the ophthalmic laser therapy apparatus using the control data for this overall incision geometry and, additionally, the overall incision geometry can optionally be represented pictorially on an indication apparatus. An ophthalmic laser therapy apparatus for these purposes is described below.

In this case, the control data for an ophthalmic laser therapy apparatus can contain geometric data for setting the position of the focus in a processing volume in the cornea of the patient's eye in the spatial directions of x, y, z and power data for each focal position.

As an alternative thereto, control data can also be produced only for the pictorial representation on an indication apparatus, which facilitates an overlay on the real image of the patient's eye, i.e., for example, on an indication apparatus of a surgical microscope or of a video microscope. In this case, the pictorial representation thus is not an additional visualization of an operation running automatically in any case but an active aid for the manual operation implemented by the surgeon, in which the appropriate incisions are made by means of a surgical knife along the pictorial indication of the overall incision geometry on the indication apparatus of the surgical microscope or of the video microscope, which has been overlaid with the real image of the eye. In a special embodiment of an indication apparatus, the overall incision geometry can be projected directly onto the cornea of the patient's eye in the process, for example with the aid of visible light, and thus be made directly visible there.

The control data for creating a pictorial indication, by contrast, can be purely geometric data, possibly with an indication of a degree of a partial penetration of the cornea: While the access incision has to be guided through the entire cornea (optionally with a small residual thickness, which is subsequently penetrated manually during suctioning or during the introduction of the intraocular lens), arcuate incisions can be implemented to different depths. Thus, as a rule, there is only a partial cut or penetration into the cornea by way of such arcuate incisions.

Moreover, the planning device can be configured to establish from the instructions for the use of a specific intraocular lens control data for creating a pictorial indication of an orientation of the specific intraocular lens on the indication apparatus, which is preferably configured to also provide a real image of the patient's eye during the process and to overlay the indication of the orientation on the real image, and/or control data for producing a text indication or for the announcement.

The established control data are then output via the interface to the ophthalmic laser therapy apparatus and/or to the indication apparatus, where said control data find use in a control unit of the ophthalmic laser therapy apparatus and/or of the indication apparatus.

An ophthalmic laser therapy apparatus can include: —a laser device with a laser source for producing a pulsed laser beam, in particular a femtosecond or picosecond laser beam, —a focusing apparatus for focusing the pulsed laser beam at a focus and—a scanning apparatus for scanning the focus of the pulsed laser beam in a tissue of the patient's eye, in particular in the cornea, which also contains the limbus as transition region between cornea and sclera.

In embodiments of a planning device, the control data for the control unit of the ophthalmic laser therapy apparatus can describe a scanning pattern of focal spots of the focus of the pulsed laser beam for the overall incision geometry, along which the tissue can be cut and/or modified by means of photodisruption.

Such a scanning pattern describes at least one cut surface that is filled by the focal spots of the focus of the pulsed laser beam moving along the scanning pattern in such a way that a complete or incomplete separation of the tissue in this cut surface occurs. Thus, to this end, the scanning pattern takes account of the necessary spacing of the focal spots of the focus of the pulsed laser beam and the position thereof in relation to one another: In the case where a complete separation is desired, a relatively small maximum distance of the focal spots from one another (for a given power of the pulsed laser beam) is necessary; an incomplete separation occurs as a result of a greater spacing of the focal spots and, finally, no separation of the tissue is possible any more in the case of a very large spacing of the focal spots.

Moreover, such a scanning pattern can describe a tissue region that is microstructured by the pulsed laser beam, said tissue region being filled by the focal spot of the focus of the pulsed laser beam moving along the scanning pattern in such a way that the tissue of this tissue region is modified, but not separated, in an effective focal region around the focal spot of the pulsed laser. Such microstructured tissue regions likewise are able to influence a corneal curvature such that in principle—should an ophthalmic laser therapy apparatus be used for the operation and, in particular, for the astigmatism correction—microstructured tissue regions also can contribute to changing the astigmatism of the patient's eye.

In a particular configuration, the planning device is embodied to take account of a deformation of the cornea of the patient's eye by an apparatus for immobilizing the patient's eye during a laser therapy when producing the control data for an ophthalmic laser therapy apparatus such that the planned overall incision geometry is present after implementing the surgical intervention in the non-deformed cornea.

This is advantageous in the case of a deformation of the cornea as a result of affixing the patient's eye to the ophthalmic laser therapy apparatus by means of a patient interface while the laser therapy is carried out. By way of example, such a patient interface can be a contact glass or a liquid patient interface.

It is advantageous if provision is made for the supplied target data of the planning unit moreover to comprise a start of the iterative method in respect of intraocular lens, access incision and/or one or more arcuate incisions.

In principle, the arcuate incisions are determined by the astigmatism axes and are influenced by the position of the access incision. Thus, the surgeon can check the characterization data of the patient's eye in respect of astigmatism and, using this, place a start or start combination approximately in the region in which he expects good results in respect of the residual astigmatism. Hence, he may possibly significantly reduce the number of iteration steps that are required until a correction combination with which the residual astigmatism is smaller than a maximum residual astigmatism is found.

Further, according to embodiments of the disclosure, a planning device is advantageous, whose supplied target data moreover comprise data relating to exclusion regions in the cornea of the patient's eye, which also contains the limbus as transition region between cornea and sclera, in which no incisions may be produced.

By way of example, regions in which an operation has already been carried out may be excluded from a renewed access and thus a renewed treatment. Since there is always a greater number of solutions for an astigmatism correction, relating to the arrangement of the access incision in relation to the arcuate incisions and relating to the number, size and depth thereof, a solution for the arrangement of the incisions in which a maximum residual astigmatism is not exceeded still can be found, as a rule, when an exclusion region is specified.

Also, this can exclude regions in which incisions in the cornea are not indicated or are only carried out in an emergency because they contribute to a particular extent to the vision of the patient's eye.

Here, in one disclosed embodiment of the planning unit, hierarchizing regions of the cornea is possible: Regions can be characterized as preferred incision regions, standard incision regions, regions in which incisions in the cornea should only take place if other correction combinations are not possible or as absolute exclusion regions.

A planning device is advantageous if it is configured to establish all correction combinations from: (i) the multiplicity of available intraocular lenses and their orientation, which may be saved in a database, for example, (ii) the multiplicity of available variants of an access incision and its position, and (iii) from the multiplicity of available variants of one or more arcuate incisions and their position.

The planning device can be configured to finally select the maximum correction combination, which has the smallest residual astigmatism, therefrom and to save this as the pattern of the overall incision geometry and the instructions for the use of the specific intraocular lens.

In this configuration of the planning device, establishing an astigmatism correction is encoded in such a way that the entire trial option space can be run through and a residual astigmatism can be established for each combination in order to subsequently find that correction combination from the totality of the correction combinations found when run through the trial option space which, when used, yields a minimum value for the residual astigmatism of the patient's eye, i.e., the minimum value of the entire trial option space.

In order to correct a regular astigmatism as far as possible, it is of some advantage if the multiplicity of available intraocular lenses for the planning device comprises toric intraocular lenses. It is completely or almost completely possible to correct the regular astigmatism, i.e., the component of the overall astigmatism of the patient's eye for which the plane of maximum corneal curvature and of minimal corneal curvature are perpendicular to one another, by means of such a toric intraocular lens. The component of the overall astigmatism of the patient's eye, which is referred to as "irregular astigmatism", remains.

In order to establish the corrective effect of a combination of an intraocular lens and its orientation, the access incision and its position and size in the cornea and of the one or more arcuate incisions and their position, size and depth in the cornea, approximation methods are usually used in turn for each specific combination in order to be able to make a statement about the residual astigmatism.

A planning device configured to use at least one of the methods outlined below to establish the corrective effect of the combination of an intraocular lens and its orientation, the access incision and its position and size in the cornea of the patient's eye and the one or more arcuate incisions and their position on the astigmatism of the patient's eye is particularly advantageous: (i) ray tracing, which is a numerical individual ray calculation method, in which the superposition of the effect of a multiplicity of individual rays, which each start at a defined point and at a defined angle relative to the optical system and are refracted at each optical surface according to Snell's law, is considered; (ii) the Gaussian optics method, a method from geometric optics, in which a calculation of the system is implemented by means of a mathematical formula under the assumption that the rays intersect the optical axis at very flat angles. (iii) one or more arcuate incision nomograms.

Here, in the present case, the following formula of the intraocular lens, for example, can be used: $P=[n_v/(A_L-C)]-[K/(1-K_xC/n_A)]$, where P: power of the target intraocular lens (in dioptre) K: average dioptric power of the central cornea (in dioptre) $A_L$: axial length of the eye (in millimetres) C: effective lens position (in millimetres), i.e., the distance between the anterior corneal surface and the central plane of the intraocular lens $n_v$: refractive index of the vitreous humour $n_A$: refractive index of the aqueous humour. See Hoffer K J. "Modern IOL power calculations: Avoiding error and planning for special circumstances. Focal Points: Clinical Modules for Ophthalmologists." San Francisco: American Academy of Ophthalmology; 1999, module 12). However, other IOL calculation formulae are also conventional (Barrett Suite, Haigis Suite, Hoffer® Q, Holladay 2, SRK®/T); these may be used depending on the axial length of the eye and the refractive error and these are preferably selectable in this case.

Useful for a planning device are provided arcuate incision nomograms, which can be chosen by the user. Well known manual arcuate incision nomograms are encoded in the planning device, like the Donnenfeld nomogram and the Nichamin nomogram. It is further possible to incorporate other nomograms for the particular use of the user.

In a further configuration of the planning device, a measuring device is connected to the interface, said measuring device producing the characterization data of the patient's eye from the measurement of the patient's eye and supplying said characterization data to the planning device, wherein the measuring device preferably comprises one or more of the following apparatuses: autorefractor, refractometer, corneal topograph, keratometer, placido disc reflection (for corneal topography), wavefront measuring device, optical coherence tomography (OCT) device, preferably for both the anterior and posterior corneal surface, Scheimpflug camera, options for measuring the axial length of the eye by means of partial coherence interferometry, for example, for measuring the depth of the anterior chamber, for measuring the corneal diameter (also known as white-to-white measurement), ultrasonic imaging system, microscope. It goes without saying that the number of measuring devices which may be connected to the interface for supplying data is not limited to just one at a time, but data from very different measurement devices may be produced and transmitted to the planning device via the interface.

Useful is a planning device for establishing an astigmatism correction in cataract surgery, either as described above or a general such device, which is comprising an interface for supplying characterization data of a patient's eye, comprising data about an astigmatism of the patient's eye, and which is embodied to produce, from the supplied data, a pattern of an overall incision geometry in the cornea of the patient's eye, said pattern including at least the position and the geometric data of an access incision and an arcuate incision or a plurality of arcuate incisions, which is further embodied to improve the astigmatism correction by post-surgical results of precedent astigmatism corrections carried out using the planning device.

The inventive planning device allows surgeons to configure the software so that the software itself can pre-determine which option the surgeon will most likely want to employ. The planning device is also configured to take into account the results of precedent cataract surgery results.

In an embodiment, the planning device comprises a special interface to gather post-operation results of the patients (refraction and residual astigmatism) to verify and improve the quality and to evaluate specific adjustment factors. Further, in an advantageous embodiment, an up-load into a cloud-based data storage and processing system for optimization via deep learning is possible.

Also useful is a planning device for establishing an astigmatism correction in cataract surgery, either as described above or a general such device, which comprises an interface for supplying characterization data of a patient's eye, comprising data about an astigmatism of the patient's eye, and which is embodied to produce, from the supplied data, a pattern of an overall incision geometry of incisions in the cornea of the patient's eye, said pattern including at least the position and the geometric data of an access incision and an arcuate incision or a plurality of arcuate incisions, which is further embodied to configure the astigmatism correction by entering an adjustment factor for the vertical and for the horizontal axis.

The planning device is thus further configurable by surgeons with experience using any published nomogram for arcuate incisions, who may determine that their own results differ such that their own patients may be systematically over or under corrected if the nomogram is used as originally encoded. Disclosed embodiments of the planning device allow surgeons (or other competent users) to enter an adjustment factor (configuration) for the vertical (i.e. with-the-rule, WTR), and the horizontal (i.e. against-the-rule, ATR) net astigmatism axis. This adjustment is a percentage of the standard nomogram arc length. The planning device performs a trigonometric analysis to determine the appropriate adjustment for any oblique astigmatic error. This novel system allows surgeons to fine-tune their own predictions over time based on actual patient outcomes.

Such a planning device, when configured to use arcuate incision nomograms to establish a corrective effect, is then advantageously further embodied to improve an arcuate incision nomogram by post-surgical results of precedent astigmatism corrections carried out using the planning device and that arcuate incision monogram, and/or is advantageously further embodied to configure an arcuate incision nomogram by entering an adjustment factor for the vertical and for the horizontal axis.

In a special embodiment, the planning device comprises an interface for access to a cloud-based data storage for data collection and analysis via deep learning, and feedback to the planning device. This can be important for an option of the planning device allowing continuous improvement of the results.

Useful is a planning device which provides the interface for entering the characteristic data of a plurality of available IOLs and/or a databank containing said data.

In an embodiment, the planning device provides an interface for the user (i.e. the surgeon) to vary individual parameters such as IOL toric correction, IOL axis, arcuate incision characteristics, access incision characteristics, thus triggering a re-calculation of the correction, so that surgeon can direct the calculation towards favoured correction combinations.

Disclosed is a planning device for establishing an astigmatism correction in cataract surgery, either as described above or a general such device, which is comprising an interface for supplying characterization data of a patient's eye, comprising data about an astigmatism of the patient's eye, and which is embodied to produce, from the supplied data, a pattern of an overall incision geometry of incisions in the cornea of the patient's eye, said pattern including at least the position and the geometric data of an access incision and an arcuate incision or a plurality of arcuate incisions, which is configured to determine an incision conflict and to check the creation of asymmetric arcuate incisions along the same axis and/or a movement of the access incision by a rotation around the optical axis for an avoidance of the incision conflict.

For Incision Conflict Avoidance, the planning device can be unique in that it progresses through a series of computations to find the most effective means of avoiding an incision conflict while optimizing the overall astigmatism correction. Unlike other systems that simply suggest a single, larger incision rather than the original paired incisions, an embodiment of the invention first determines if the conflict can be avoided by creating asymmetric arcuate incisions along the same axis. It also checks to see if moving the access incision to 90 degrees, 180 degrees (right eyes), or 0 degrees (left eyes) can completely eliminate the astigmatism and avoid an incision conflict. It also calculates the appropriate location for an access incision which is 90 degrees off of the arcuate incision axis. Surgeons can configure the system to allow or disallow asymmetric incisions and moving the access incision. The planning device also provides an option for a single incision. Each of the options provided are presented to the surgeon with a calculated percentage of astigmatism eliminated and a calculated residual astigmatism power and axis.

That means that the user, e.g. the surgeon may, among others, set each of the following configurations to influence the performance of the planning device: (i) percentage of adjustment of the arc length for with-the-rule (WTR) net astigmatism, especially in conjunction with at least one of the following nomograms: the Donnenfeld nomogram; the Nichamin nomogram; (ii) percentage of adjustment of arc length for against-the-rule (ATR) net astigmatism, especially in conjunction with at least one of the following nomograms: the Donnenfeld nomogram; the Nichamin nomogram; (iii) define if yes or no asymmetric arc lengths for incision conflict avoidance shall be used; (iv) define if the access incision (i.e. the phacoemulsification incision) shall be relocated for incision conflict avoidance.

The results may further be displayed such that the user is presented with the proposed arcuate incision parameters based on a selected nomogram and an incision avoidance algorithm, preferably with a table that displays the results of the various conflict avoidance options.

An improved astigmatism correction may also be obtained with a planning device for establishing an astigmatism correction in cataract surgery, either as described above or a general such device, which is comprising an interface for supplying characterization data of a patient's eye, comprising data about an astigmatism of the patient's eye, and which is embodied to produce, from the supplied data, a pattern of an overall incision geometry of incisions in the cornea of the patient's eye, said pattern including at least the position and the geometric data of an access incision and an arcuate incision or a plurality of arcuate incisions, wherein data about an astigmatism of the patient's eye comprise a measured anterior corneal astigmatism and a theoretical or measured posterior corneal astigmatism.

This leads to an assessment of Total Corneal Astigmatism: Most arcuate incision nomograms and also most planning devices use the anterior corneal astigmatism (measured by keratometry) and occasionally the surgically induced astigmatism (SIA) as well to determine the appropriate arcuate incision plan. However, the initial nomogram is based on the results of prior studies that used this same methods (keratometry and SIA). But in addition, outcome data are collected to make use of a potentially more accurate measure of total corneal astigmatism by adding a theoretical or measured posterior corneal astigmatism component for use with arcuate incision nomograms. This approach also incorporates any astigmatism correction provided by a toric intraocular lens (IOL) to determine a net astigmatism that has to be treated with arcuate incisions. Unlike other planning devices, embodiments of the planning device according to the invention can incorporate this net corneal astigmatism into the arcuate incision planning process to provide more predictable postoperative outcomes.

Another improved astigmatism correction may be obtained by a planning device for establishing an astigmatism correction in cataract surgery, either as described above or a general such device, which is comprising an interface for supplying characterization data of a patient's eye, comprising data about an astigmatism of the patient's eye, and which is embodied to produce, from the supplied data, a pattern of an overall incision geometry of incisions in the cornea of the patient's eye, said pattern including at least the position and the geometric data of an access incision and an arcuate incision or a plurality of arcuate incisions, wherein a length of an arcuate incision is based on a net astigmatism and a patient's age.

Increasing patient age is associated with decreasing corneal compliance that can also affect the results.

An ophthalmic laser therapy apparatus for treating a tissue of the patient's eye can comprise: (i) a laser device with a laser source for producing a pulsed laser beam, a focusing apparatus for focusing the pulsed laser beam at a focus and a scanning apparatus for scanning the focus of the pulsed laser beam in a tissue of the patient's eye, in particular in a cornea, which also contains the limbus as transition region between cornea and sclera, for cutting and/or modifying the tissue along a scanning pattern of focal spots of the focus of the pulsed laser beam, said pattern being determined by control data, (ii) a control unit for controlling the ophthalmic laser therapy apparatus by means of the control data, and (iii) a planning device for producing the control data as described above.

Optionally, the pulsed lasers used for cutting in the cornea are femtosecond or picosecond lasers. However, excimer lasers can also be used.

Optionally, the ophthalmic laser therapy apparatus moreover comprises a measuring device for producing characterization data of the patient's eye, in particular a measuring device from the following group: autorefractor, refractometer, keratometer, wavefront measuring device, optical coherence tomography (OCT) device, preferably for both the anterior and posterior corneal surface, Scheimpflug camera, options for measuring the axial length of the eye by means of partial coherence interferometry, for example, for measuring the depth of the anterior chamber, for measuring the corneal diameter (also known as white-to-white measurement), ultrasonic imaging system, microscope. Hence, establishing an astigmatism correction for a cataract operation or during a cataract operation is completely integrable into an ophthalmic laser therapy apparatus.

As an alternative or at the same time, an above-described planning apparatus may, however, also be part of a surgical microscope or a video microscope.

Disclosed is a planning method for establishing an astigmatism correction in cataract surgery, a pattern of an overall incision geometry of incisions in the cornea of the patient's eye, which also contains the limbus as a transition region between cornea and sclera, said pattern including at least the position and the geometric data of an access incision and an arcuate incision or a plurality of arcuate incisions, and instructions for the use of a specific intraocular lens, said instructions comprising a type of intraocular lens and an orientation of this intraocular lens in the patient's eye, is produced by virtue of (i) characterization data of a patient's eye, comprising data of an astigmatism of the patient's eye, and target data, comprising a maximum residual astigmatism and a variant of a cataract-surgical intervention and/or data relating to the precision of this cataract-surgical intervention being established and introduced into the planning method, (ii) in order to establish, in each step of an iterative method, a corrective effect of a combination of (a) an intraocular lens and its orientation from a multiplicity of available intraocular lenses of varying strengths of correction of sphere and astigmatism (b) an access incision and its position (in the cornea including the limbus) from a multiplicity of available variants of an access incision, and (c) one or more arcuate incisions and their position from a multiplicity of available variants of one or more arcuate incisions on the astigmatism of the patient's eye and to determine a residual astigmatism, (iii) wherein the available variants of the access incision and of the one or more arcuate incisions are assigned to the variant of the cataract-surgical intervention and/or the data relating to the precision of the cataract-surgical intervention, (iv) and the iterative method is continued until the residual astigmatism is less than or equal to the maximum residual astigmatism for a correction combination, (v) and this correction combination is saved as the pattern of the overall incision geometry and the instructions for the use of the specific intraocular lens.

In a planning method, moreover, control data for an astigmatism correction for an ophthalmic laser therapy apparatus for producing this overall incision geometry and/or control data for creating a pictorial indication of the overall incision geometry on an indication apparatus, in particular on an indication apparatus of a surgical microscope or a video microscope, for overlay purposes on an image of the patient's eye are established from the pattern of the overall incision geometry.

Such an indication apparatus can thus be a 2D or 3D screen of a video camera of a video microscope or of a surgical microscope, or a data injection module into the eyepiece of a surgical microscope, by means of which the eye can be indicated, preferably in real time, such that the patient's eye can be observed during the process with an overlay of the overall incision geometry. Alternatively, the indication apparatus can also be an indication unit, e.g., a 2D or 3D screen, which is set up in such a way that it can easily be perceived by the surgeon; however, it is not contained in a surgical microscope or in a video microscope but it is present at a spatial distant therefrom and connected therewith by way of communication paths.

As a further alternative, an indication apparatus can also be configured in such a way that the overall incision geometry is projected directly onto the cornea of the patient's eye, for example using visible light.

Immobilizing the patient's eye and/or continuously tracking selected structures of the patient's eye in a spatially resolved manner is suggested in any case in which an overall incision geometry is intended to be overlaid on the display of the patient's eye or else intended to be realized by means of an ophthalmic laser therapy apparatus, depending on structures of the patient's eye with a defined position in the patient's eye.

Using these control data, the ophthalmic laser therapy apparatus is controllable and/or the pictorial indication of the overall incision geometry is overlaid in the indication device on a real established image of the patient's eye in such a way that the overall incision geometry is producible by cutting along the pattern, i.e., in automated fashion using the ophthalmic laser therapy apparatus or manually using a surgical knife that is guided by the surgeon.

Moreover, control data for creating a pictorial indication of an orientation of the specific intraocular lens on the indication apparatus, on which the patient's eye preferably can also be observed during the process, and/or control data for producing a text indication or for an acoustic announcement are established from the instructions for the use of a specific intraocular lens.

The established control data are then output via the interface to an ophthalmic laser therapy system and/or an indication apparatus.

Furthermore, it is advantageous if, in an embodiment of the planning method, a deformation of the cornea of the patient's eye by an apparatus for immobilizing the patient's eye during a laser therapy, in particular a deformation of the cornea as a result of fixing the patient's eye to the ophthalmic laser therapy apparatus by means of a patient interface, is taken into account when producing the control data for an ophthalmic laser therapy apparatus such that the planned overall incision geometry is present, after the procedure, in the non-deformed cornea after such a laser therapy.

In order to reduce the number of iteration steps, the option of manually selecting a start of the iterative method in respect of intraocular lens, access incision and/or one or more arcuate incisions is provided in a planning method. The more experienced the surgeon selecting the start, the faster a correction combination, i.e., a combination which does not exceed a maximum residual astigmatism, can be found.

It is further advantageous if the user (i.e. the surgeon) can vary individual parameters such as IOL toric correction, IOL axis, arcuate incision characteristics, access incision characteristics, thus triggering a re-calculation of the correction, so that surgeon can direct the calculation towards favoured correction combinations.

It is also advantageous if exclusion regions, in which no incisions may be produced, in the cornea of the patient's eye, which also contains the limbus as transition region between cornea and sclera, are also taken into account in disclosed embodiments of the planning method when establishing the astigmatism correction.

By way of example, regions in which an operation has already been carried out may be specified in order to be excluded from a renewed access within the scope of the planning method.

Also, this can specify regions in which incisions in the cornea are not indicated or only carried out in extremely rare cases, for example the primary incision in the nasal position (around 0° or right eyes or 90° on left eyes).

Here, in one variant of the planning method, hierarchizing regions of the cornea is possible: Regions can be characterized as preferred incision regions, as standard incision regions, as regions in which incisions in the cornea should only take place if other correction combinations are not possible or as absolute exclusion regions. The regions are then used in this order for the purposes of establishing the correction combination (the last category remaining completely excluded).

In an advantageous planning method, one or more (e.g., all) of the following are used to establish all correction combinations: (i) the multiplicity of available intraocular lenses and their orientation, (ii) the multiplicity of available variants of an access incision and its position, and (iii) the multiplicity of available variants of one or more arcuate incisions and their position.

The maximum correction combination, which has the smallest residual astigmatism, is finally established from this plurality of established correction combinations and saved as the pattern of the overall incision geometry and the instructions for the use of the specific intraocular lens.

Thus, advantageously, all possible combinations of intraocular lens and its orientation, access incisions and their size and position and arcuate incisions and their number, size and position are tested here in order to establish the best possible correction combination.

Furthermore, a planning method in which at least one of the methods outlined below is used to establish the corrective effect of the combination of an intraocular lens and its orientation, the access incision and its position and size in the cornea and the one or more arcuate incisions and their position, size and depth on the astigmatism of the patient's eye (and preferably taking account of an additional surgically induced astigmatism of the patient's eye) is particularly advantageous: —Ray tracing, the Gaussian optics method, one or more arcuate incision nomograms.

In a configuration of the planning method, the characterization data of the patient's eye are produced from a measurement of the patient's eye, wherein the characterization data are preferably established by means of one or more of the following measurements: autorefractive measurement, refractometric measurement, keratometric measurement, corneal topography via placido disc reflection, wavefront measurement, optical coherence tomography (OCT), preferably both for the anterior and posterior corneal surface, Scheimpflug method, measuring the axial length of the eye, e.g., by means of partial coherence interferometry, measuring the depth of the anterior chamber, measuring the corneal diameter (also known as white-to-white measurement), ultrasound imaging, microscopic measurement.

Useful is a planning method for establishing an astigmatism correction in cataract surgery, either as described above or a general such method, wherein a pattern of an overall incision geometry of incisions in the cornea of the patient's eye, said pattern including at least the position and the geometric data of an access incision and an arcuate incision or a plurality of arcuate incisions, is produced by virtue of characterization data of a patient's eye, comprising data of an astigmatism of the patient's eye, which is further improved by analysis of post-surgical results of precedent astigmatism corrections carried out using the planning method.

Also particularly useful is a planning method for establishing an astigmatism correction in cataract surgery, either as described above or a general such method, wherein a pattern of an overall incision geometry of incisions in the cornea of the patient's eye, said pattern including at least the position and the geometric data of an access incision and an arcuate incision or a plurality of arcuate incisions, is produced by virtue of characterization data of a patient's eye, comprising data of an astigmatism of the patient's eye, which is further configured by entering an adjustment factor for the vertical and for the horizontal axis.

Such a planning method, when configured to use arcuate incision nomograms to establish a corrective effect, is then advantageously further embodied to improve an arcuate incision nomogram by analysis of post-surgical results of precedent astigmatism corrections carried out using the planning method and that arcuate incision monogram, and/or is advantageously further embodied to configure an arcuate incision nomogram by entering an adjustment factor for the vertical and for the horizontal axis.

The planning method may thus further be configured by surgeons with experience using any published nomogram for arcuate incisions, who may determine that their own results differ such that their own patients may be systematically over or under corrected if the nomogram is used as originally encoded. The surgeon is allowed to enter an adjustment factor for the vertical (i.e. with-the-rule, WTR), and the horizontal (i.e. against-the-rule, ATR) net astigmatism axis. This adjustment is a percentage of the standard nomogram arc length. A trigonometric analysis is performed to determine the appropriate adjustment for any oblique astigmatic error. This allows a fine-tuning of the surgeon's predictions over time based on actual patient outcomes.

In an advantageous embodiment of the planning method the post-surgical results of precedent astigmatism corrections carried out using the planning method are uploaded to a cloud-based data storage and processing platform for analysis of data from a plurality of sources for further improvement of the planning method.

A planning method is of further advantage, if the data used for further improvements is analysed using artificial intelligence and deep-learning methods.

In a further advantageous planning method for establishing an astigmatism correction in cataract surgery, either as described above or a general such method, wherein a pattern of an overall incision geometry of incisions in the cornea of the patient's eye, said pattern including at least the position and the geometric data of an access incision and an arcuate incision or a plurality of arcuate incisions, is produced by virtue of characterization data of a patient's eye, comprising data of an astigmatism of the patient's eye, an incision conflict is determined and the creation of asymmetric arcuate incisions along the same axis and/or a movement of the access incision by a rotation around the optical axis are checked for an avoidance of the incision conflict.

For Incision Conflict Avoidance, the planning method is unique in that it progresses through a series of computations to find the most effective means of avoiding an incision conflict. Unlike other methods that simply suggest a single, larger incision rather than the original paired incisions, an embodiment of the planning method first determines if the conflict can be avoided by creating asymmetric arcuate incisions along the same axis. It also checks to see if moving the access incision to 90 degrees, 180 degrees (right eyes), or 0 degrees (left eyes) can completely eliminate the astigmatism and avoid an incision conflict. It also calculates the appropriate location for an access incision which is 90 degrees off of the arcuate incision axis. Surgeons can configure the planning method to allow or disallow asymmetric incisions and moving the access incision. The planning method also provides an option for a single incision. Each of the options provided are presented to the surgeon with a calculated percentage of astigmatism eliminated and a calculated residual astigmatism power and axis.

An improved astigmatism correction may also be obtained using a planning method for establishing an astigmatism correction in cataract surgery, either as described above or a general such method, wherein a pattern of an overall incision geometry of incisions in the cornea of the patient's eye, said pattern including at least the position and the geometric data of an access incision and an arcuate incision or a plurality of arcuate incisions, is produced by virtue of characterization data of a patient's eye, comprising data of an astigmatism of the patient's eye, wherein data about an astigmatism of the patient's eye comprise a measured anterior corneal astigmatism and a theoretical or measured posterior corneal astigmatism.

A Total Corneal Astigmatism is assessed by this planning method. Most arcuate incision nomograms and also most planning methods use the anterior corneal astigmatism (measured by keratometry) and occasionally the surgically induced astigmatism (SIA) as well to determine the appropriate arcuate incision plan. In an embodiment of the planning method, however, the initial nomogram is based on the results of prior studies that used these same methods (keratometry and SIA). But in addition, outcome data are collected to make use of a potentially more accurate measure of total corneal astigmatism by adding a theoretical or measured posterior corneal astigmatism component for use with arcuate incision nomograms. This approach also incorporates any astigmatism correction provided by a toric intraocular lens (IOL) to determine a net astigmatism that has to be treated with arcuate incisions. Unlike other planning methods, disclosed planning methods can incorporate this net corneal astigmatism into the arcuate incision planning process to provide more predictable postoperative outcomes.

Another improved astigmatism correction may be obtained by a planning method for establishing an astigmatism correction in cataract surgery, either as described above or a general such method, wherein a pattern of an overall incision geometry of incisions in the cornea of the patient's eye, said pattern including at least the position and the geometric data of an access incision and an arcuate incision or a plurality of arcuate incisions, is produced by virtue of characterization data of a patient's eye, comprising data of an astigmatism of the patient's eye, wherein a length of an arcuate incision is determined based on a net astigmatism and a patient's age.

Embodiments of a computer program product can comprise program code which, when executed on a computer, executes the above-described planning method for establishing an astigmatism correction in cataract surgery and/or which is readable on an above-described planning device for establishing an astigmatism correction in cataract surgery, in particular by a processor of such a planning device, and preferably on such a planning device for consecutively controlling an ophthalmic laser therapy apparatus and/or an indication apparatus with control data produced in the process, and which, when executed by the planning device, produces control data to operate the ophthalmic laser therapy apparatus and/or the indication apparatus.

Here, an indication apparatus can be a visual indication apparatus, such as that of a surgical microscope or of a video microscope, or an indication apparatus for text indication, or else an indication apparatus for acoustic indications.

A computer program product according to the invention can be stored on a non-transitory computer-readable medium.

The aforementioned features and those discussed below can be used not only in the combinations specified but also in other combinations or on their own.

FIG. 1a schematically shows the ophthalmic laser therapy apparatus 1 (i.e., a system) comprising a first embodiment of the planning device (i.e., a system). In this variant, it comprises at least two devices or modules. A laser device L (also called a "cutting device") emits the pulsed laser beam 2 on to the patient's eye 3. Here, the laser device L operates completely automatically; i.e., the laser device L, following an appropriate start signal, starts the deflection of the laser beam 2 and, in the process, produces cut surfaces 24, modified or micro-structured areas or modified or microstructured tissue regions in the cornea 16, including the limbus 17 as transition region between cornea 16 and sclera 14, which are built as will still be described below. The control data required for the operation are received by the laser device L in advance as a control data record from a planning device P via communication paths not denoted in any more detail, such as control lines, for example. Naturally, the communication can also be implemented in wireless fashion. As an alternative to direct communication, it is also possible to arrange the planning device P in spatially separated fashion from the laser unit L and to provide a corresponding data transmission channel. The transmission is preferably implemented prior to the operation of the laser device L. Although the present application discusses cutting in terms of laser device L, any suitable cutting device (e.g., a manually operated scalpel, an automatically operated scalpel, a manually operated laser, an automatically operated laser, etc.) may be applied.

Optionally, the control data record is transmitted to the laser device L of the ophthalmic laser therapy apparatus 1 via an interface S2 of the planning device P. An operation of the laser device L can be blocked until a valid control data record is present at the laser device L. A valid control data record can be a control data record that, in principle, is suitable for use with the laser device L of the ophthalmic laser therapy apparatus 1. However, additionally, the validity can also be linked to further tests being passed, for example whether specifications about the ophthalmic laser therapy apparatus 1, e.g., an apparatus serial number, or about the patient, e.g., a patient identification number, which are additionally stored in the control data record, correspond to other specifications that, for example, are read at the ophthalmic laser therapy apparatus 1 or entered separately as soon as the patient is in the correct position for the operation of the laser device L.

The planning device P produces the control data or the control data record, which is made available to the laser device L for implementing the operation, from the supplied data. Firstly, these are characterization data, which comprise data relating to an astigmatism of the patient's eye 3, which were established for the patient's eye 3 to be treated by means of a measuring device M and which are supplied via an interface S1 for supplying characterization data of the planning device P. Secondly, target data is supplied by a further interface S1, said target data comprising a maximum residual astigmatism and a variant of a cataract-surgical intervention and data relating to the precision of this cataract-surgical intervention. They are transmitted to the planning device P via the interface S1 by an input apparatus E. Some of the data—such as the maximum residual astigmatism, for example—can be entered freely into this input apparatus. Another part, such as the variant of the cataract-surgical intervention, can be marked in the input device E.

In the present exemplary embodiment, the measurement data originate from an independent measuring device M, which had previously measured the patient's eye 3. Naturally, the measuring device M can transmit the corresponding measurement data to the planning device P in any suitable way. A direct radio or wired link of the measuring device M to the ophthalmic laser therapy apparatus 1 in respect of the data transmission, which can be used in one variant, is advantageous in that the use of incorrect measurement data can be excluded with the greatest possible reliability.

In the present case, the data of the various intraocular lenses 5 (IOL) are stored in an internal database of the planning device P. In other cases, however, they can be likewise supplied from an external database via an interface S1 of the planning device P of the ophthalmic laser therapy apparatus 1.

The control data produced by the planning device P determine the scanning pattern 15 of the focus 7 of the laser device L in the tissue of the patient's eye 3, in particular in the cornea 16 thereof, the ophthalmic laser therapy apparatus 1 being controllable by means of said control data in such a way that the access incision 18 and the arcuate incision or the arcuate incisions 19 are producible—and if the control data are used on the ophthalmic laser therapy apparatus 1—they are also produced.

The transmission of the supplied data can be implemented by means of memory chips (e.g., by USB or memory stick), magnetic storage units (e.g., disks), wirelessly by radio (e.g., WLAN, UMTS, Bluetooth) or in wired fashion (e.g., USB, FireWire RS232, CAN bus, Ethernet, etc.). Naturally, the same applies in respect of the data transmission between planning device P and laser device L.

Figure 1B:
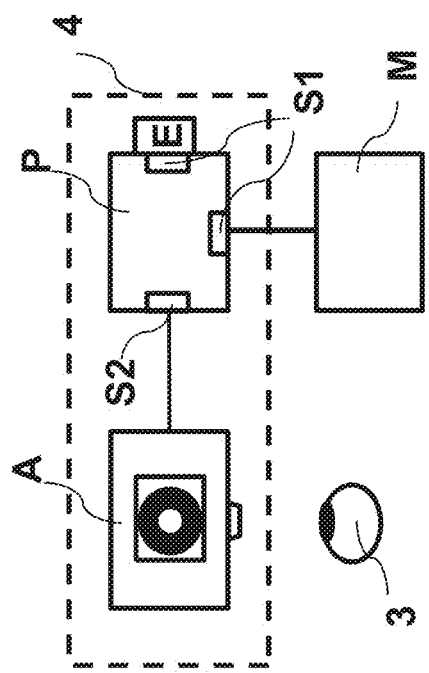
FIG. 1b shows a diagram of a surgical microscope comprising a second planning device.

FIG. 1b illustrates a diagram of a surgical microscope comprising a second embodiment of the planning device. The data supply by the interfaces S1, in particular from an independent measuring device M and an input device E, is implemented in a manner analogous to what was described in FIG. 1a.

The data output to the indication apparatus A of a surgical microscope 4 is once again implemented by way of an interface S2.

In this case, the planning device P produces, firstly, the control data for the pictorial indication of the overall incision geometry of incisions in the cornea 16 (which also contains the limbus 17 as transition region between cornea 16 and sclera 14) on the indication apparatus A of the surgical microscope 4, said overall incision geometry comprising the position and the geometric data of an access incision 18 and at least one arcuate incision 19, and, secondly, the control data with the instructions for the use of a specific intraocular lens 5. Both information items—the pictorial indication of the overall incision geometry and the instructions for the use of the specific intraocular lens 5—can be produced at the same time or in timely succession on the indication apparatus A of the surgical microscope 4.

The first embodiment of the planning device P, which is part of the ophthalmic laser therapy apparatus according to FIG. 1a, and the second embodiment of the planning device P, which is part of the surgical microscope 4 according to FIG. 1b, can each be part of a common planning device P which, firstly, supplies a corresponding ophthalmic laser therapy apparatus 1 with the appropriate control data for producing the access incision 18 and arcuate incisions 19 and, secondly, produces the necessary control data with instructions for the use of a specific intraocular lens 5, in particular for the use of a specific toric intraocular lens 5, for the indication apparatus A of a surgical microscope 4 and transmits said control data to the latter. Optionally, this common planning device P can also generate additional control data for the pictorial indication of the overall incision geometry on the indication apparatus A, in addition to the control data for producing the overall incision geometry of access incision 18 and arcuate incisions 19 by means of the ophthalmic laser therapy apparatus 1. Here, once again, surgical microscope 4 and ophthalmic laser therapy apparatus 1 can form an overall system, in which both apparatuses and also the planning device P, and optionally the measuring device M, are integrated.

Figure 2:
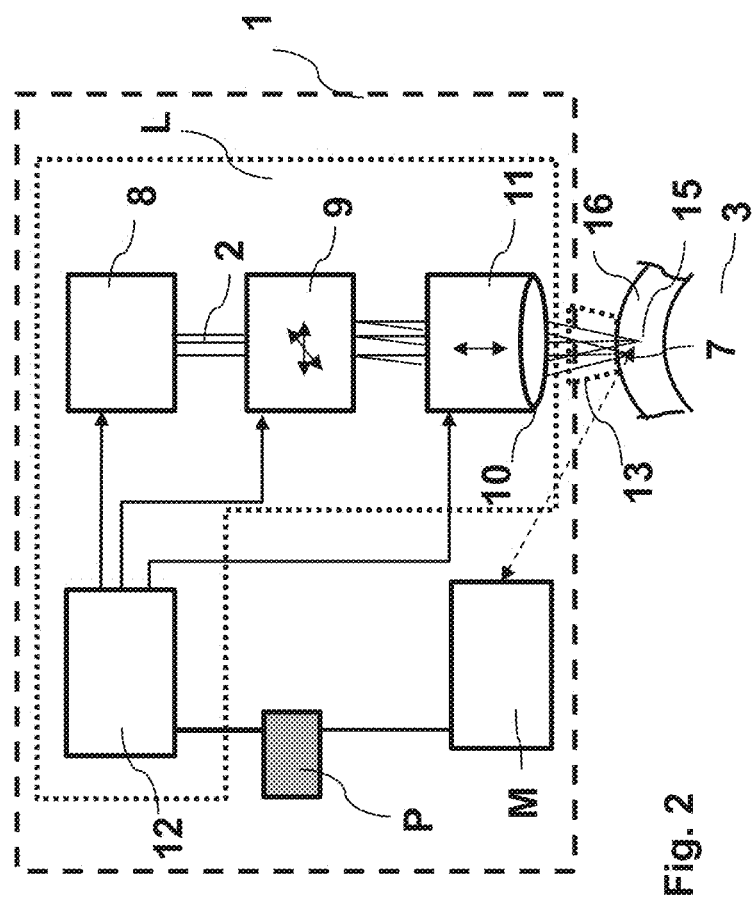
FIG. 2 shows a second ophthalmic laser therapy apparatus comprising a third planning device.

FIG. 2 shows, once again schematically, a second embodiment of the ophthalmic laser therapy apparatus 1 with a third embodiment of the planning device P, in which a laser device L and a measuring device M are integrated. This facilitates repeated access to characterization data of the patient's eye 3. The planning device P, which satisfies the functions already described above, is integrated, at least temporarily, into the ophthalmic laser therapy apparatus 1 and is in direct communication with the measuring device M and the control unit 12 of the laser device L.

In this example, the elements of the ophthalmic laser therapy apparatus 1 and, in particular, of the laser device L comprised thereby are specified, but, in this case, too, only drawn to the extent that they are required for understanding the focal adjustment. The pulsed laser beam 2, a femtosecond laser beam in this specific example, is focussed at a focus 7 in the cornea 16 and the position of the focus 7 in the cornea 16 is adjusted such that, for the purposes of producing cut surfaces and hence for the purposes of producing the overall incision geometry made of access incision 18 and arcuate incision or arcuate incisions 19 in the cornea 16 of the patient's eye 3 at different positions, i.e., the focal spots 6 of the focus 7 along the scanning pattern 15 of this focus, energy from pulses of the laser radiation is introduced into the tissue of the cornea 16 of the patient's eye 3 and hence the tissue is separated by means of photodisruption. The laser beam 2 is provided as pulsed radiation by a femtosecond laser 8. Here, the cornea 16 of the patient's eye 3 is immobilized by means of a patient interface 13 to the ophthalmic laser therapy apparatus 1.

An x-y-scanner 9, which is realized by two substantially orthogonal deflecting galvanometer mirrors in one variant, deflects the pulsed laser beam 2 emanating from the laser source 8 in two dimensions. Consequently, the x-y-scanner 9 brings about an adjustment of the position of the focus 7 substantially perpendicular to the main direction of incidence of the pulsed laser beam 2 into the cornea 16. In addition to the x-y-scanner 9, a z-scanner 11 is provided for adjusting the depth position, said z-scanner being embodied as an adjustable telescope, for example. The z-scanner 11 ensures that the z-position of the position of the focus 7, i.e., the position thereof along the optical axis of incidence, is modified. The z-scanner 11 can be disposed upstream or downstream of the x-y-scanner 9. The coordinates denoted below by x, y, z therefore relate to the deflection of the position of the focus 7.

The assignment of the individual coordinates to spatial directions is not essential for the functional principle of the ophthalmic laser therapy apparatus 1; however, for the purposes of simpler description, z always denotes the coordinate along the optical axis of incidence of the pulsed laser beam 2, and x and y denote two mutually orthogonal coordinates in a plane perpendicular to the direction of incidence of the laser beam 2. Naturally, a person skilled in the art knows that the position of the focus 7 in the cornea 16 can also be described in three dimensions by other coordinate systems; in particular, does not necessarily need to be a rectangular coordinate system. Thus, it is not mandatory for the x-y-scanner 9 to deflect about axes that are perpendicular to one another; rather, it is possible to use any scanner that is able to adjust the focus 7 in a plane not containing the axis of incidence of the laser beam 2. Consequently, it is also possible to use oblique-angled coordinate systems, or else non-Cartesian coordinate systems.

For the purposes of controlling the position of the focus 7, the x-y-scanner 9 and the z-scanner 11, which together realize a specific example of a three-dimensional focus adjustment device 9, 11, are actuated by a controller 12 via lines not denoted in any more detail. The same applies to the laser source 8. The controller 12 ensures a suitable synchronous operation of the laser source 8 and the three-dimensional focus adjustment device 9, 11, which is realized in exemplary fashion by the x-y-scanner 9 and the z-scanner 11, and so the position of the focus 7 in the cornea 16 is adjusted in such a way that, ultimately, the overall incision geometry in the cornea 16 of the patient's eye 3 is achieved by scanning predetermined target points, i.e., the focal spots 6, on the scanning pattern 15, respectively by irradiating the pulsed laser beam 2 at each of these target points, by way of a photodisruption process caused hereby and, consequently, the production of the cut surface 24 or a plurality of cut surfaces, which are formed by the overall incision geometry of access incision 18 and arcuate incision or arcuate incisions 19 in the cornea 16, is achieved by way of a plurality of such target points.

The controller 12 operates according to predetermined control data, which predetermine the target points for the focal adjustment. As a rule, the control data are combined in a control data record. In one embodiment, the latter predetermines the coordinates of the target points as a pattern, wherein the sequence of the target points in the control data record sets the stringing together of the focal positions and hence, consequently, a trajectory—the scanning pattern 15. In one embodiment, the control data record contains the target points as specific manipulated variables for the focal position adjustment mechanism, e.g., for the x-y-scanner 9 and the z-scanner 11. In one embodiment, it also contains all data required for operating the laser source 8 in addition to the geometric data of the respective target points. For the purposes of preparing the ophthalmic treatment, i.e., before the proper surgical treatment can be implemented, the target points and, preferably, the sequence thereof in the pattern are determined in order to be able to produce the overall incision geometry of access incision 18 and arcuate incision 19 or arcuate incisions 19 in the cornea 16 of the patient's eye 3.

Thus, the surgical intervention is planned in the process to the effect of control data being established for the ophthalmic laser therapy apparatus 1, the application of which then obtains an overall incision geometry of access incision 18 and arcuate incision 19 or arcuate incisions 19 in the cornea 16 of the patient's eye 3. This is achieved by embodiments of planning device P and embodiments of the planning method.

FIG. 3a illustrates the results of astigmatism characterization of a patient's eye 3. In relation to these astigmatism data of the patient's eye 3, FIG. 3b shows an established position of a toric intraocular lens 5 to be inserted and possible incisions (access incision 18 and arcuate incision 19) in a patient's eye, by means of which the established astigmatism of the patient's eye 3 can be corrected to the best possible extent. However, the effect of the intraocular lens 5 and of the access incision 18 and the arcuate incisions 19 on the astigmatism of the patient's eye 3 have not yet been taken into account in this illustration.

FIG. 4a shows a further illustration of an astigmatism characterization of a patient's eye 3. In FIG. 4b, the position of an intraocular lens 5 in relation to the patient's eye 3 is specified and the correcting influence thereof on the astigmatism of the patient's eye 3 has already been taken into account: Consequently, the residual astigmatism can be reduced to zero in the upper region of the patient's eye 3; a residual astigmatism (the irregular part of the astigmatism) remains in the lower region of the patient's eye 3. As shown in FIG. 4c, said residual astigmatism can be also reduced to approximately zero by way of an appropriate position of an access incision 18 and an arcuate incision 19.

Figure 5:
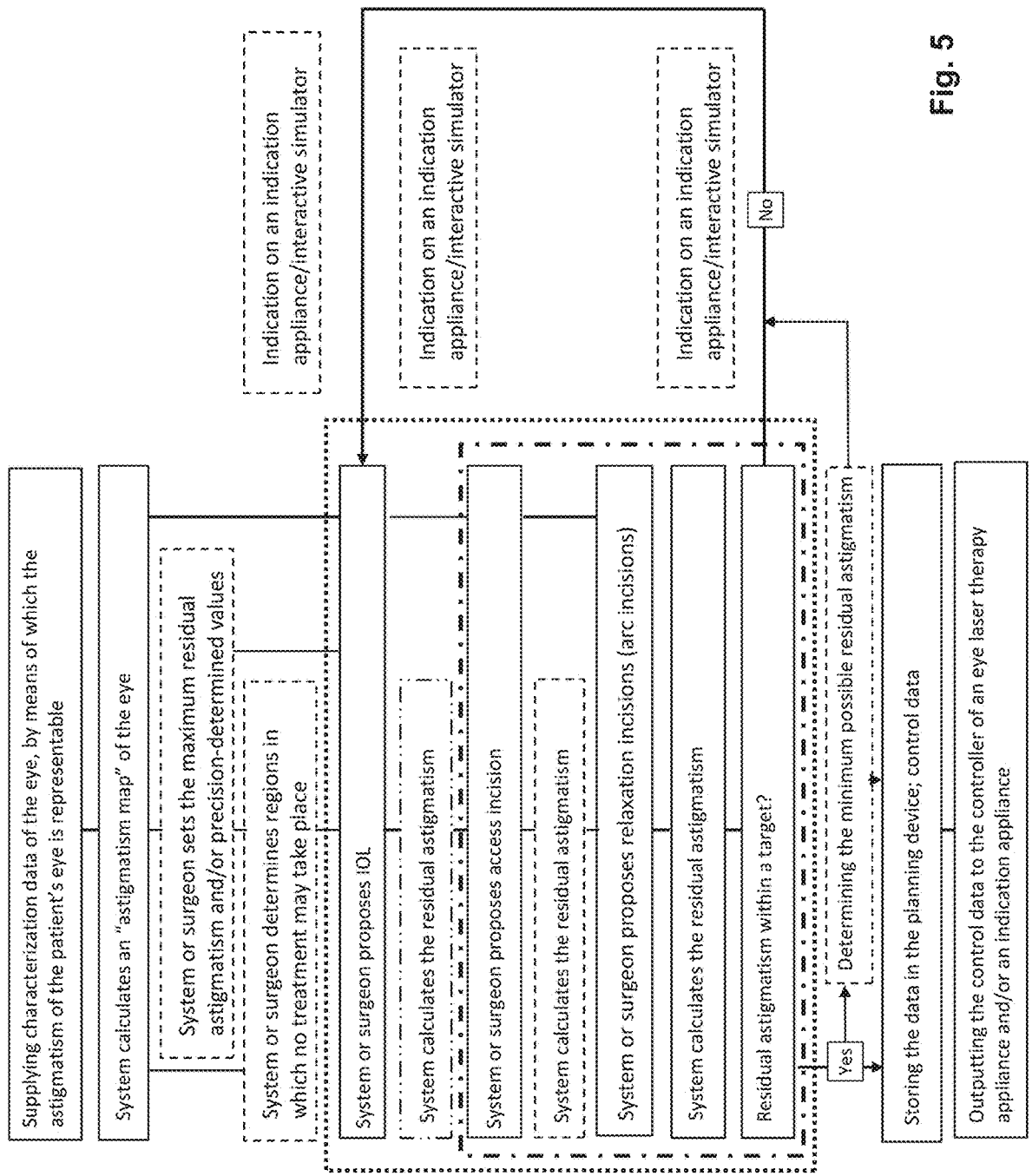
FIG. 5 shows a general diagram of a planning method in various possible configurations, which is encoded in a planning device.

FIG. 5 illustrates a general diagram of a planning method in various possible configurations, which is encodable in a planning device P, as an example. Full frame lines shown obligatory steps in this case; different types of dashed lines highlight optional steps.

Thus, initially, characterization data of the patient's eye 3, by means of which the astigmatism of this patient's eye is representable, are supplied. Moreover, further target data are gathered; in particular, a maximum residual astigmatism is supplied. This value can be determined by the surgeon or else it can be supplied as a fixed value from a database, which is linked to the planning device P, in a simple variant. Additionally, further data—such as a desired precision when creating access incision 18 and arcuate incision or arcuate incisions 19—can be specified. Specifying the desired precision (or the precision that is possible depending on the surgical method) has an influence on the number of available variants of the access incision 18 or of the arcuate incision or incisions 19, which, during the iterative establishment of a correction combination of the corresponding intraocular lens 5, access incision 18 and arcuate incision(s) 19, with which the residual astigmatism of the patient's eye 3 is less than a predetermined maximum residual astigmatism, are tested, which precision forms a measure for the increment to the next variant of an access incision 18 or arcuate incision 19.

Optionally, the surgeon can moreover specify regions of the cornea 16, in which no incisions may be placed.

These data are therefore supplied to an iterative calculation routine, in which the corrective effect on the present astigmatism of the patient's eye 3 are established from a combination of an intraocular lens 5 and its orientation selected from a multiplicity of available intraocular lenses 5, from an access incision 18 (with its geometric properties) and its position selected from a multiplicity of available variants of an access incision 18, and from one or more arcuate incisions 19 (with their geometric properties and number) and their position selected from a multiplicity of available variants of one or more arcuate incisions 19, and a residual astigmatism is determined.

A suitable intraocular lens 5 (IOL), which corrects the regular astigmatism of the patient's eye 3 to the best possible extent, is sensibly sought at first in this case. Often, this is a toric intraocular lens 5. Then, the access incision and the arcuate incision or incisions and their (number and) position in relation to one another are varied in order to calculate a residual astigmatism from the corresponding combination. If the latter is within a target, i.e., less than a predetermined maximum residual astigmatism, the corresponding combination is a possible correct combination which contains the pattern of the overall incision geometry and the instructions for the use of the established specific intraocular lens 5. The iterative calculation routine can then be terminated and the corresponding correction combination can be stored and the above-described control data can be established therefrom, an ophthalmic laser therapy apparatus 1 being able to be operated therewith in order to produce this overall incision geometry and/or control data for creating a pictorial indication of the overall incision geometry on an indication apparatus A, in particular on an indication apparatus A of a surgical microscope 4 or a video microscope, to be overlaid on an image of the patient's eye 3, and instructions for the use of the specific intraocular lens 5 being able to be provided using said control data—in a pictorial indication of an orientation of the specific intraocular lens 5 on the indication apparatus A and/or in a text indication or an acoustic announcement.

Here, a surgeon can accelerate the iterative calculation routine by the prescription of an intraocular lens 5, by the prescription of a preferred access incision 18 and/or by the prescription of one or more preferred arcuate incisions 19. It is also possible to test through the entire trial option space of intraocular lens, access incision and arcuate incisions if the specification in relation to the maximum residual astigmatism is refined with instructions after searching the minimal possible value (and consequently no fixed value is predetermined by the user).

Indications relating to the status of the simulations can be made at various points during the course of the calculation routine.

The established data are saved assigned to the corresponding patient or patient's eye 3 and can, in principle, be used immediately.

Figure 6A:
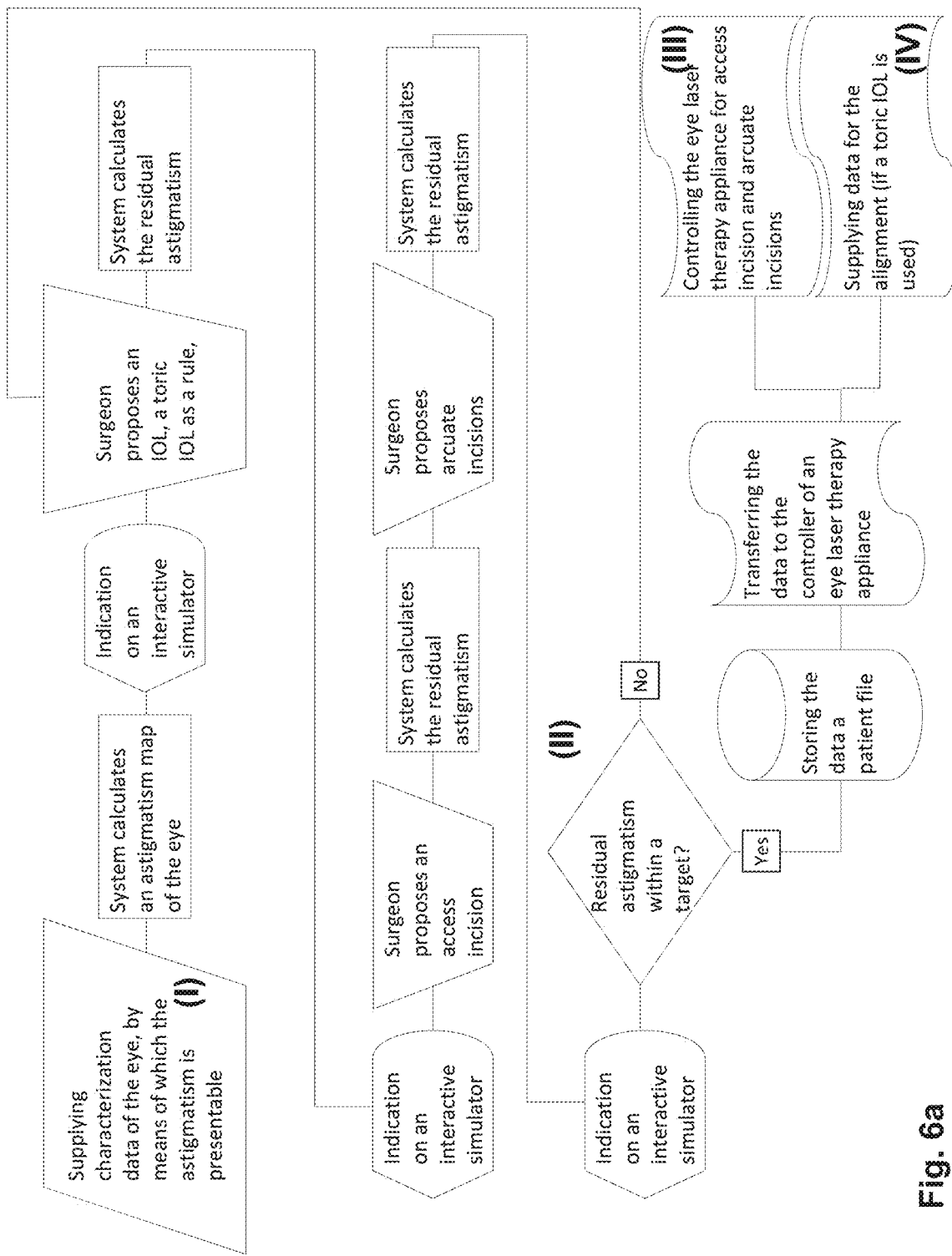
FIG. 6a shows an example of a specific planning method and FIG. 6b shows the apparatuses involved in the planning method.

By contrast FIG. 6a shows an example of a specific planning method:

From the supplied characterization data of a patient's eye 3 in relation to its astigmatism, the system calculates the astigmatism map of the patient's eye 3, which is displayed on an interactive simulator screen. The surgeon can predetermine an intraocular lens 5 and a first residual astigmatism (for the use of the predetermined intraocular lens 5) is calculated for the patient's eye 3 and displayed on the interactive simulator screen. The same is implemented for the access incision 18 and the arcuate incisions (also referred to as "arc incisions").

Figure 6B:
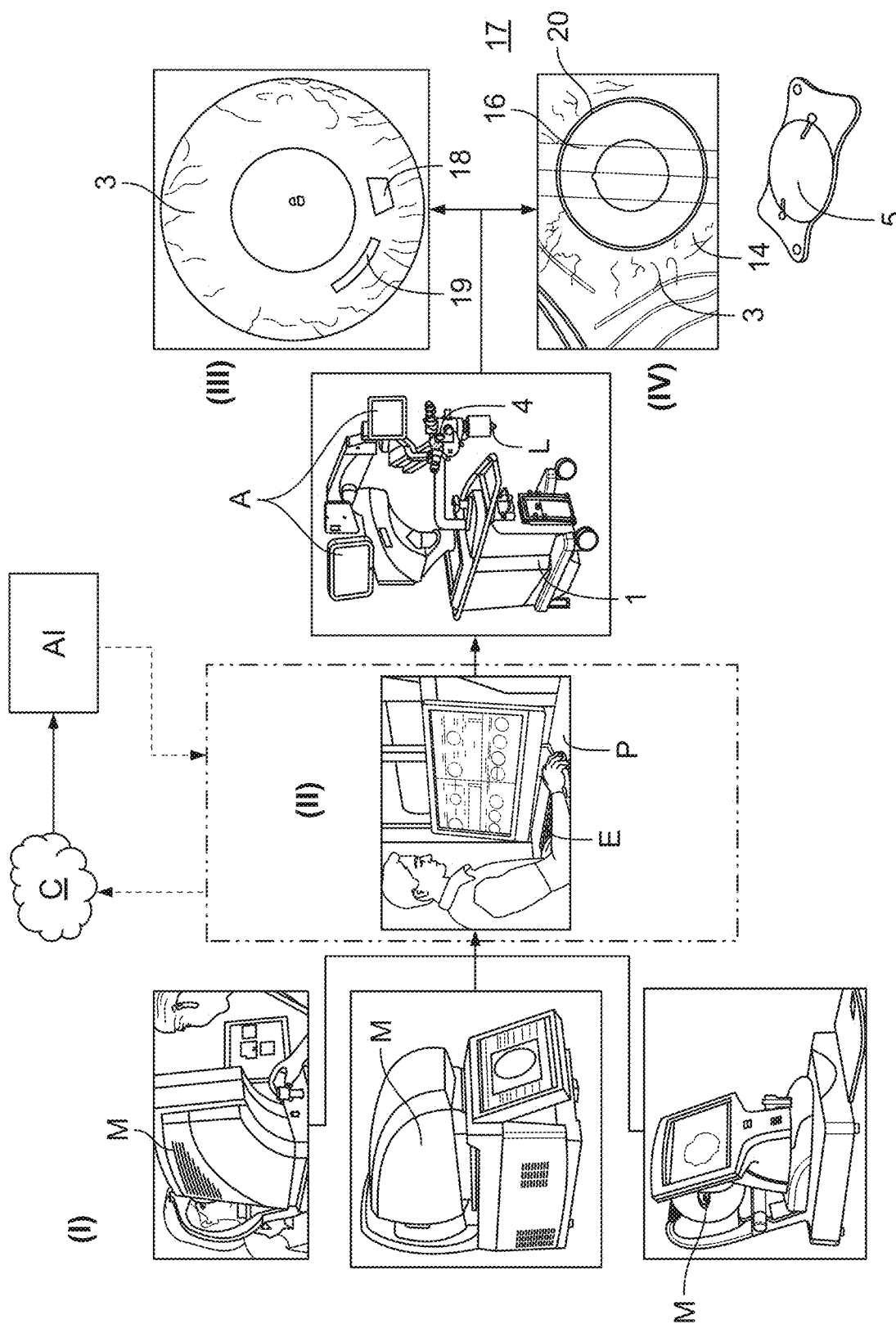

The residual astigmatism of a combination established thus is compared to a target (e.g., to a maximum permissible residual astigmatism). If this target is not satisfied, the next combination is calculated. In this example, the surgeon can intervene again and again and "guide" the combinations to be tested if, by looking at the display of the interactive simulator screen, he perceives that the interactive calculation routine is advancing in a direction which they would prefer not to be continued. The individual phases of the planning method are specified by (I), (II), (III) and (IV) in order to be able to clarify, in FIG. 6b, what apparatuses are involved in the planning method at what point: Possible measuring devices M, by means of which characterization data of the patient's eye can be established in a first section (I), include, for example, the "IOL Master 700" (with which the overall keratometry and biometry of the eye can be established), a surface topography measuring device ("AT-LAS") or the "i.Profiler", which carries out a wavefront analysis. These characterization data are supplied to the planning device P (II), which also comprises an input apparatus E. The planning device P creates the control data for the operation of an ophthalmic laser therapy apparatus 1, which comprises a laser device L and a surgical microscope 4 and contains a plurality of indication apparatuses A, and the planning device P transmits said control data to the ophthalmic laser therapy apparatus 1.

From the planning device P data may optionally be uploaded to a cloud-based data storage and processing platform C for analysis of data—arrived via the planning device P as well as from a plurality of sources—for further improvement of the planning method. Data in the cloud based data storage and processing platform C may preferentially be analysed using artificial intelligence and deep learning methods.

In the ophthalmic laser therapy apparatus 1 it is possible to track on a first indication means the generation of the overall incision geometry from the access incision 18 and the arcuate incision 19 in the cornea 16 of the patient's eye 3 (III). On a further indication means of the indication apparatus A, instructions for orientating 20 the specific intraocular lens 5 in the patient's eye 3 are specified in the next step (IV), the surgeon orienting themselves with the instructions for the purposes of placing said intraocular lens 5.

Figure 7:
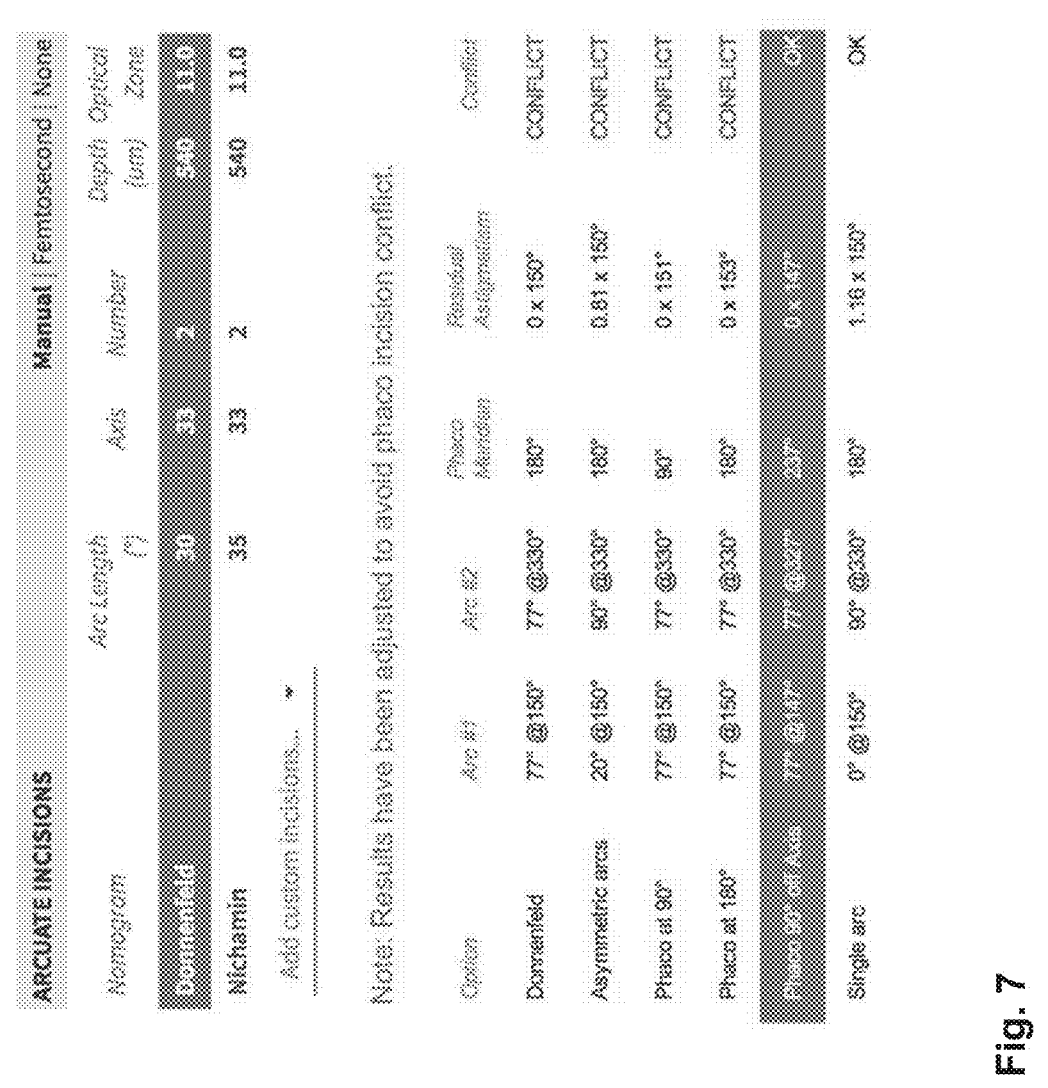

FIG. 7 illustrates the principle of conflict avoidance. Embodiments of the invention also include sophisticated analysis of potential incision conflicts and produces multiple options for conflict avoidance. For each option, the embodiments can provide the surgeon with a diagram of the proposed incisions, and a prediction of the residual astigmatism power and axis. Surgeons can select the overlap avoidance option that best meets their needs.

The results are then displayed, as shown in FIG. 7, such that the user is presented with the proposed arcuate incision parameters based on a selected nomogram and an incision avoidance algorithm, preferably with a table that displays the results of the various conflict avoidance options.

Preferred start data: For a net astigmatism after planned cataract surgery, with or without a toric IOL, the anterior corneal astigmatism (keratometry measurements), the posterior corneal astigmatism (directly measured or theoretical), the surgically induced astigmatism (i.e. the impact of the access incision) and the toricity of the IOL is needed.

In a simplified way, the net astigmatism must be calculated for the following access incision (phaco incision) locations: (i) Surgeon default location (meridian) for right or left eye (ii) 90 degree meridian (iii) 180 degree meridian for right eyes (iv) 0 degree meridian for left eyes (v) 90 degrees off (added to or subtracted from) the net astigmatism axis if the surgical induced astigmatism is 0.00. (a) For left eyes: must be less than 105 or greater than 285 degrees. (b) For right eyes: must be between 75 and 255 degrees.

The mathematical analysis of these elements to produce the net astigmatism is performed by a state of the art toric calculator, which might be incorporated into the planning device or used as an external facility.

Finally, an example shall be given for access incision conflict avoidance calculations, using nomograms.

STEP 1: Configuration adjustments. —The recommended arc length for each nomogram is adjusted by the surgeon's configuration. —Arc lengths cannot exceed nomogram maximums or minimums. —Adjustment formula: —If the net astigmatism axis (NA) is >90, move it to the 0-90 degree quadrant with the following formula: (90−(NA−90)). —Convert new axis from degrees to radians (X)−vertical net astigmatism axis WTR=configured adjustment (%) at 90 degrees÷100−horizontal net astigmatism axis ATR=configured adjustment (%) at 180 or 0 degrees÷100− Final adjustment to arc length=square-root [(ATR*cos X)$^2$+ (WTR*sin X)$^2$]

STEP 2: Percentage of astigmatism corrected by each nomogram proposed arc length—Predicted astigmatism correction with proposed arc length=PAC−Calculated net astigmatism after phacoemulsification=N−Percentage of astigmatism corrected=(PAC/N)*100

STEP 3: Conflict determination—Determine if the proposed arcuate incisions for each nomogram conflict with the default access incision. —A conflict exists if the edge of the arcuate incision is within 10 degrees of the edge of the access incision.

STEP 4: Asymmetric incision calculations

If the default access incision creates no conflict, no adjustment is needed. —Otherwise, reduce the length of the arcuate incision that conflicts with the access incision to give a 10 degree buffer between the 2 incisions. —If this can be achieved with an incision of less than the nomogram's minimum arc length, then the conflicting incision will be that length. —If reducing the incision to the minimum arc length does not avoid the conflict, the conflicting incision will remain at the minimum length. —Increase the length of the opposite (paired) incision by the same amount that the other incision was reduced. —If this can be achieved with an incision of less than the nomogram's maximum arc length, then the paired incision will be that length. —If the paired incision length exceeds the maximum allowed arc length for the nomogram, the paired incision will be set at the maximum. —Calculate the percentage of astigmatism corrected. —Asymmetric incision arc length=AAL−Nomogram proposed arc length=NAL−percentage of astigmatism corrected by nomogram=N %−percentage astigmatism corrected by asymmetric incision=(AAL/NAL)×N %

STEP 5: Move Access incision—For each nomogram, determine if either arcuate incision conflicts with an access incision at the following locations: —90 degrees—180 degrees (right eyes only)—0 degrees (left eyes only)—90 degrees off (added to or subtracted from) the net astigmatism axis if the SIA is 0.00—Left eyes: must be less than 105 or greater than 285 degrees—Right eyes: must be between 75 and 255 degrees These parameters are set to that a cataract surgeon can technically perform the surgery in these locations. —Calculate the percentage of astigmatism corrected (same method as described for asymmetric incisions)

STEP 6: Convert to a Single Arcuate Incision—For each nomogram, determine if either proposed arc conflicts with the access incision. —If no conflict exists, no single arc is proposed. —Otherwise, eliminate the arc that conflicts and double the size of the paired (non-conflicting) arc. —If the doubled paired arc exceeds the maximum arc length for the nomogram, use the maximum as the new arc length. —Calculate the percentage of astigmatism corrected (same method as described for asymmetric incisions).

STEP 7: Determine best option for an arcuate incision that eliminates incision conflict and maximizes the percentage of astigmatism correction. —If the default access incision creates no conflict, the default is the best answer. —Asymmetric incisions are suggested only if the surgeon has configured this to be a possible option. —Moving the access incision is suggested only if the surgeon has configured this to be a possible option. —Preference is given to access incision locations closest to the surgeon's default access incision location. —Preference is given to options that correct the most astigmatism.

A therapy system can include any of the devices (i.e., systems) discussed herein, such as a laser system and a processing system. The processing system can include one or more processors configured to automatically perform any of the methods (e.g., operations, functions, etc.) disclosed herein. Therefore, the processing system can include planning device P, measuring device M, etc. Processors, and therefore the processing system, are configured to perform a method (e.g., operation) at least when one or more of the processors are configured to communicate with memory storing code embodying the method and to implement the stored code. The processing system can be distributed across multiple computing environments or housed in a unitary structure. The memory can include any combination of computer-readable media such as volatile memory and non-volatile memory. The non-volatile memory can include hard drives, optical disks, etc.

The aforementioned features, which are explained in various exemplary embodiments, can be used not only in the combinations specified in an exemplary manner but also in other combinations or on their own, without departing from the scope of the present application. A description of an apparatus of device relating to method features is analogously applicable to the corresponding method with respect to these features, while method features correspondingly represent functional features of the apparatus or device described.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

While embodiments of the invention have been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention or disclosure refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

We claim:

1. A therapy system comprising:
   a processing system comprising one or more processors configured to:
   receive an initial astigmatism condition of the eye;
   receive a target final astigmatism condition of the eye;
   generate, based on the initial and target final astigmatism conditions, an eye incision pattern, wherein the one or more processors are configured to generate the eye incision pattern by iterating through a plurality of potential corrective combinations, each of the potential corrective combinations being defined by: an intraocular lens selected from a plurality of intraocular lens options, an access incision selected from a plurality of access incision options, and an arcuate incision selected from a plurality of arcuate incision options;
   wherein at least one of (i) and (ii) are present:
   (i) the therapy system comprises a cutting device and the one or more processors are configured to control the cutting device based on the generated eye incision pattern;
   (ii) the therapy system comprises a display and a microscope and the one or more processors are configured to:
   present on the display, a live video feed of the eye captured by the microscope;
   overlay, onto the live video feed, at least a portion of the generated eye incision pattern.

2. The therapy system of claim 1, wherein the one or more processors are further configured to:
   project, for each iterated potential corrective combination, a final astigmatism condition of the eye based on: the initial astigmatism condition, the selected intraocular lens, the selected access incision, and the selected arcuate incision;
   compare, for each iterated potential corrective combination, the projected final astigmatism condition of the eye with the target final astigmatism condition of the eye;
   select at least one of the potential corrective combinations based on the comparisons; and
   set the generated eye incision pattern based on the selected at least one potential corrective combination.

3. The therapy system of claim 1, wherein each of the potential corrective combinations is further defined by an orientation of the selected intraocular lens, the orientation being selected from a plurality of intraocular lens orientation options.

4. The therapy system of claim 1, wherein the one or more processors are configured to control the cutting device based on the generated eye incision pattern by:
   selecting one of the potential corrective combinations based on the target final astigmatism condition;
   causing the cutting device to cut, into the eye tissue, an access incision based on the access incision of the selected corrective combination; and
   causing the cutting device to cut, into the eye tissue, an arcuate incision based on the arcuate incision of the selected correct combination.

5. The therapy system of claim 1, wherein the one or more processors are further configured to:
   select one of the potential corrective combinations;
   project a surgery-induced temporary deformation of the eye;
   modify, based on the projected eye deformation, the access incision of the selected corrective combination and the arcuate incision of the selected corrective combination; and
   cause the cutting device to cut, into the eye tissue, an incision based on the modified access incision and an incision based on the modified arcuate incision.

6. The therapy system of claim 1, wherein the one or more processors are further configured to receive the initial astigmatism condition of the eye by:
   receiving one or more measured dimensions of the eye, and
   determining the initial astigmatism condition based on the received measurements.

7. The therapy system of claim 1, comprising a measuring device, the one or more processors being configured to control the measuring device, the measuring device comprising a device selected from the group consisting of: a/an autorefractor, refractometer, keratometer, placido disc reflection, wavefront measuring device, optical coherence tomography (OCT) device, preferably for both the anterior and posterior corneal surface, Scheimpflug camera, options for measuring the axial length of the eye, for measuring the depth of the anterior chamber, for measuring the corneal diameter, ultrasonic imaging system, and microscope.

8. A therapeutic method comprising:
   receiving an initial astigmatism condition of an eye;
   receiving a target final astigmatism condition of the eye;
   generating, based on the initial and target final astigmatism conditions, an eye incision pattern by iterating through a plurality of potential corrective combinations, each of the potential corrective combinations being defined by:
   an intraocular lens selected from a plurality of intraocular lens options,
   an access incision selected from a plurality of access incision options, and
   an arcuate incision selected from a plurality of arcuate incision options; and
   cutting the eye based on the eye incision pattern.

9. The method of claim 8, further comprising:
   projecting, for each iterated potential corrective combination, a final astigmatism condition of the eye based on: the initial astigmatism condition, the selected intraocular lens, the selected access incision, and the selected arcuate incision;
   comparing, for each iterated potential corrective combination, the projected final astigmatism condition of the eye with the target final astigmatism condition of the eye;
   selecting at least one of the potential corrective combinations based on the comparisons; and
   setting the generated eye incision pattern based on the selected at least one potential corrective combination.

10. The method of claim 8, wherein each of the potential corrective combinations is further defined by an orientation of the selected intraocular lens, the orientation being selected from a plurality of intraocular lens orientation options.

11. The method of claim 8, further comprising cutting based on the generated eye incision pattern by:

selecting one of the potential corrective combinations based on the target final astigmatism condition;

cutting, into the eye tissue, an access incision based on the access incision of the selected corrective combination; and cutting, into the eye tissue, an arcuate incision based on the arcuate incision of the selected correct combination.

12. The method of claim 8, further comprising:
selecting one of the potential corrective combinations;
projecting a surgery-induced temporary deformation of the eye;
modifying, based on the projected eye deformation, the access incision of the selected corrective combination and the arcuate incision of the selected corrective combination; and
cutting, into the eye tissue, an incision based on the modified access incision and an incision based on the modified arcuate incision.

13. The method of claim 8, further comprising receiving the initial astigmatism condition of the eye by determining the initial astigmatism condition of the eye based on measurements received from a device selected from the group consisting of: a/an autorefractor, refractometer, keratometer, placido disc reflection, wavefront measuring device, optical coherence tomography (OCT) device, preferably for both the anterior and posterior corneal surface, Scheimpflug camera, options for measuring the axial length of the eye, for measuring the depth of the anterior chamber, for measuring the corneal diameter, ultrasonic imaging system, and microscope.

14. The method of claim 8, further comprising:
capturing an image of the eye; and
presenting, on an electronic display, at least a portion of the generated eye incision pattern overlaid onto the captured image.

15. The method of claim 8, further comprising:
capturing a live video feed of the eye; and
presenting, on an electronic display, at least a portion of the generated eye incision pattern overlaid onto the live video feed.

16. The method of claim 15, further comprising continuously and automatically realigning the generated eye incision pattern with the live video feed.

17. A non-transitory computer readable medium storing program code configured to cause a processing system comprising one or more processors to perform the method of claim 8.

18. A therapeutic method, comprising:
selecting a corrective combination by iterating through a plurality of potential corrective combinations, each combination being defined by an intraocular lens selected from a plurality of intraocular lens options, a natural access incision selected from a plurality of access incision options, and a natural arcuate incision selected from a plurality of arcuate incision options;
projecting a surgically-induced temporary deformation of an eye;
modifying both of the natural access incision and the natural arcuate incision of selected corrective combination based on the projected temporary deformation; and
cutting the eye based on the modified access and arcuate incisions.

19. The method of claim 18, wherein after the temporary eye deformation dissipates and the eye returns to a natural condition, the modified access and arcuate incisions previously cut into the temporarily deformed eye respectively transform into the natural access and arcuate incisions.

20. The method of claim 18, wherein each of the corrective combinations is defined by an orientation of the selected intraocular lens, the orientation being selected from a plurality of intraocular lens orientation options; and the cutting is performed with a laser system configured to cut eye tissue with a focused laser beam.

* * * * *